US005712161A

United States Patent [19]
Koezuka et al.

[11] Patent Number: 5,712,161
[45] Date of Patent: Jan. 27, 1998

[54] METHOD FOR CULTURING ANIMAL CELLS IN COLLAGEN DROPS ON A SUPPORT

[75] Inventors: Masahiro Koezuka, Kashiba; Naohito Kondo, Osaka; Hisayuki Kobayashi, Osaka; Hiroshi Saeki, Osaka; Keizo Tanisaka, Yamatotakada; Sachiko Oda, Yao, all of Japan

[73] Assignee: Nitta Gelatin Inc., Osaka, Japan

[21] Appl. No.: 507,418

[22] PCT Filed: Dec. 26, 1994

[86] PCT No.: PCT/JP94/02222

§ 371 Date: Aug. 24, 1995

§ 102(e) Date: Aug. 24, 1995

[87] PCT Pub. No.: WO95/18216

PCT Pub. Date: Jul. 6, 1995

[30] Foreign Application Priority Data

Dec. 30, 1993 [JP] Japan ................................. 5-351036

[51] Int. Cl.$^6$ ........................... C12N 5/00; C12N 1/02; C12N 11/04; C12Q 1/02
[52] U.S. Cl. .................. 435/382; 435/29; 435/177; 435/182; 435/395; 435/404
[58] Field of Search .................. 435/174, 177, 435/180, 182, 240.22, 29, 32, 34, 382, 395, 404

[56] References Cited

U.S. PATENT DOCUMENTS

| | | | |
|---|---|---|---|
| 4,352,883 | 10/1982 | Lim | 435/178 |
| 4,647,536 | 3/1987 | Mosbach et al. | 435/177 |
| 5,242,806 | 9/1993 | Yen-Maguire et al. | 435/32 |
| 5,356,793 | 10/1994 | Koezuka et al. | 435/32 |
| 5,543,327 | 8/1996 | Yen-Maguire et al. | 435/287.9 |

FOREIGN PATENT DOCUMENTS

| | | |
|---|---|---|
| 0447034 | 9/1991 | European Pat. Off. . |
| 3285696 | 12/1991 | Japan . |
| 412898 | 12/1991 | Japan . |
| 5336996 | 12/1993 | Japan . |
| 2565843 | 12/1996 | Japan . |
| 9117240 | 11/1991 | WIPO . |

OTHER PUBLICATIONS

International Journal of Oncology, vol. 2, No. 6, Jun. 1993 M. Koezuka et al "Drug Sensitivity Test For Primary Culture ...".

Chem. Abstracts, vol. 115, No. 15, Abstract No. 149651p Aizawa et al. "Usefulness of Collagen–Gel Matrix Culture ...".

Journal of Surgical Oncology vol. 49 No. 2 Feb. 1992, T. Furukawa et al. "Increased Drug Resistance of Cultured . . .".

"Prospective Clinical Trial of a Human Tumor Cloning System", Cancer Research, vol. 43, pp. 1926–1931, Apr. 1983.

"Tissue Culture Research", vol. 6, No. 1, 1987, (Translation of p. 100).

Barnes, et al., Analytical Biochemistry, vol. 102, pp. 255–270, 1980.

*Primary Examiner*—David M. Naff

[57] ABSTRACT

Animal cells are cultured while embedded in a collagen gel. The gel containing cells is formed by dispersing animal cells in a collagen solution, placing a drop (or drops) of the cell-containing collagen solution on a support surface and allowing the drop to gel to fix on the surface as a globular collagen gel having a convex surface. The cells are cultured by contacting the gel with a culture medium that may be serum-free or contain dextran sulfate. The drop preferably contains about 3 to about 300 microliters of the collagen solution and is about 2 mm or less in height. The cells may be precultured on a support surface having a collagen layer, released from the collagen layer by treatment with collagenase and dispersed in the collagen solution. The cells can be evaluated after culturing by staining such as with neutral red, or with fluorescein diacetate and irradiating, or by photographing cells in the collagen gel. The support surface can be a continuous ridge forming a recessed area and the drop of collagen solution is placed in the recessed area. Cancer cells can be cultured to test for sensitivity to an anticancer agent. The interaction of cells can be observed in co-culture tests where different kinds of cells are cultured simultaneously. Culturing in a drop enables using a small amount of animal cells sampled from tissue.

29 Claims, 4 Drawing Sheets

(a)

(b)

METHOD FOR CULTURING ANIMAL CELLS IN COLLAGEN DROPS ON A SUPPORT

TECHNICAL FIELD

The present invention relates to a method for culturing animal cells under embedded conditions, and in particular, it relates to a method for culturing animal cells under embedded conditions, which method is applicable to a method for testing the sensitivity to anticancer agents or a method for testing co-culture.

BACKGROUND ART

As to conventional tests for the sensitivity to anticancer or carcinostatic agents, they may be carried out using subcultured cancer cells, but methods of evaluating effects of anticancer agents upon respective individuals by utilizing so-called primary culture in which samples taken from a living body are directly cultured are widely employed.

However, when using a sample taken from a living body, only a small amount of cancer cells can be obtained. In addition, the sample contains normal cells other than cancer cells of interest and further contains many other components.

Tests for the sensitivity to anticancer agents (anticancer agent sensitivity tests) are conventionally carried out, using different anticancer agents alone or in various combinations, or changing the dose of anticancer agent to various ones, thus discovering optimum conditions. For this reason, a sample taken from a living body is divided under respective test conditions, and only an aliquot of the sample is used for each test. However, as mentioned above, if the total amount of cancer cells in the sample taken from the living body is small, the amount of cancer cells as separated for use in each test become very slight. Consequently, the accuracy of the test is lowered or a sufficient amount of samples to provide to necessary test items cannot be obtained. In addition, the proliferation of cancer cells may be inhibited even when cultured under conditions where the cancer cells are not in contact with anticancer agents, because of mass proliferation of cells other than the cancer cells, such as fibroblasts. Furthermore, the cancer cells may be difficult to distinguish from other cells when evaluating culture effect. This renders it impossible to accurately compare proliferation states of the cancer cells when in contact with the anticancer agent and when not in contact therewith.

Thus, various methods for increasing the accuracy of anticancer agent sensitivity tests have been proposed. An example of the methods includes embedding a sample containing cancer cells in a collagen gel for culturing. Because the proliferation of cancer cells is quite favorable in collagen gels, the comparison between the results of adding and not adding an anticancer agent in question is facilitated. There is another method in which the number of colonies formed upon proliferation of cancer cells is counted utilizing image analysis technique. This method is very favorable for using a sample which is taken from a living body and contains a mixture of cancer cells and fibroblasts, because this method allows a morphological distinction in a collagen gel between colonies of cancer cells formed into in-vivo-like morphology and colonies formed by the proliferation of fibroblasts contained together with the cancer cells in the sample taken from a living body. This technique, in which the collagen gel-embedded culture and the image analysis are combined, was earlier invented by the inventors of the present application and is disclosed in the specification of Japanese Patent Application No. Heisei 2-267343(Japanese Official Patent Provisional Publication (Kokai) No. Heisei 3-285696).

However, even the above-mentioned conventional technique is unsatisfactory in respect to culture technique in order to increase the accuracy of anticancer agent sensitivity tests. Increase in accuracy of anticancer agent sensitivity tests requires seeding cancer cells at a appropriate cell density even in a small amount of cancer cells and requires culturing under an environment as favorable as possible to the proliferation of cancer cells.

In a culture method in which a collagen solution containing dispersed cancer cells is poured into a culture dish to form a collagen gel layer over the entire bottom of the culture dish, the cancer cells are dispersed over the entire wide surface of the culture dish. This causes the following problems. In the case where the total amount of cancer cells is small, the accuracy of the test is lowered, cancer cells do not proliferate well, or wide fluctuations occur in the test results, because the count of the cells per unit area is reduced and because the number of the cells present within the field of view taken for image analysis is small. A large amount of cancer cells is needed for dispersing cancer cells at a sufficient density over the entire surface of a wide culture dish, but satisfactory tests cannot be carried out using a small amount of samples as obtained from living bodies. Furthermore, in the case where cancer cells present at a high density over the entire surface of a wide culture dish is cultured, it is impossible to provide an adequate amount of nutrients to the cancer cells in a collagen gel layer via the surface thereof using a culture solution which just covers the surface of the collagen gel layer. Likewise, components excreted from the cancer cells during the culturing are difficult to eliminate from the surface of the collagen gel layer into the culture solution. This means that anticancer agents are difficult to remove from the collagen gel layer even when it is attempted to wash off the anticancer agents after they have been contacted with the collagen gel layer in the culture dish for a prescribed length of time. In addition, nutrients becomes deficient soon, because the amount of the culture solution to come into contact with the collagen gel layer is considerably smaller than the gel volume.

As conventional co-culture methods, the following methods are employed: a method in which different kinds of cells are simply mixed; a method in which cells are laid into the form of multiple layers utilizing a plane culture method; a tissue culture method in which a lump of tissue is cultured as it is; and the like. However, interactions of cells cannot appropriately be evaluated, because cells as mixed for the co-culture or used in the non-separated form cannot be measured in the form separated into each one. Fibroblasts can be separated image-analytically in the conventional embedded culture method using a collagen gel, but as mentioned above this method is unsatisfactory in respect to a way of culture even if the co-culture is applied to this method.

DISCLOSURE OF THE INVENTION

OBJECTS OF THE INVENTION

An object of the present invention is to provide a method by which precise and adequate sensitivity test can be carried out even if only a small amount of animal cells can be sampled from tissue.

Another object of the present invention is to provide a method by which interactions of cells can specifically be observed and measured when different kinds of cells are cultured simultaneously.

SUMMARY OF THE INVENTION

A method for culturing animal cells under embedded conditions, according to the present invention, includes a cell dispersion step, an embedding step, and a culture step. The cell dispersion step includes a step of dispersing animal cells into a collagen solution. The embedding step includes a step of placing a drop or drops of the collagen solution on a surface of a support to allow the drop or drops to gel to form and fix on the support surface a globular collagen gel or gels having a convex surface. The culture step includes a step of culturing the animal cells by bringing a culture solution into contact with the collagen gel or gels.

DETAILED DESCRIPTION OF THE INVENTION

A method for culturing animal cells under embedded conditions, according to the present invention, includes a cell dispersion step, an embedding step, and a culture step. The cell dispersion step includes a step of dispersing animal cells into a collagen solution. The embedding step includes a step of placing a drop or drops of the collagen solution on a surface of a support to allow the drop or drops to gel to form and fix on the support surface a globular collagen gel or gels having a convex surface. The culture step includes a step of culturing the animal cells by bringing a culture solution into contact with the collagen gel or gels.

The culture method of the present invention may further include an evaluation step after the culture step.

The evaluation step may include a reagent contact step of using a reagent utilizing a biochemical reaction which is caused by the cells embedded in the collagen gel or gels.

The evaluation step may further include a photographing step of photographing the collagen gel or gels and an image analysis step of subjecting to image analysis an image which is taken in the photographing step.

The image analysis step may further include a staining step of selectively staining the cells embedded in the collagen gel or gels.

The staining step may include a live cell-staining step of selectively staining live cells in the collagen gel or gels.

The staining step may include an NR-staining step of selectively staining live cells in the collagen gel or gels with an NR-staining agent.

The NR-staining step may include a fixing step of fixing the NR-staining agent into the live cells and may further include a drying step of drying the NR-staining agent fixed in the fixing step.

In the case where the evaluation step further includes the photographing step and the image analysis step, the culture method of the present invention preferably further includes before the cell dispersion step a preliminary culture step of preculturing a preliminary culture sample containing the animal cells using the culture solution on a surface of a preliminary support with a collagen gel layer as an adhesion factor, and collecting only live cells which are adhered to the surface of the preliminary support, thus obtaining the culture sample.

The live cell-staining step may include a step of staining the live cells with an FDA-staining agent under conditions where the irradiation amount of excitation light is in a range of $1 \times 10^0$ to $1 \times 10^7$ lux.sec and where the measurement environment temperature is in a range of 1° to 15° C.

The culture method of the present invention may further include before the cell dispersion step a preliminary culture step of preculturing a preliminary culture sample containing the animal cells on a surface of a preliminary support using the culture solution, and collecting only live cells which are adhered to the surface of the preliminary support, thus obtaining the culture sample.

The preliminary support may have a cell adhesion factor which is coated on a surface of the preliminary support.

The cell adhesion factor is preferably a collagen gel layer.

The culture solution may contain dextran sulfate.

The reagent contact step may include a colorimetric analysis step of carrying out colorimetric analysis using a coloring reagent which causes a selective color reaction by metabolic activity of the live cells in the collagen gel or gels.

The reagent contact step may include a step of quantitatively analyzing substances which are contained in the cells embedded in the collagen gel or gels.

The reagent contact step may include a step of quantitatively analyzing substances which are secreted into the culture solution from the cells embedded in the collagen gel or gels.

The reagent contact step may include a staining step of selectively staining the cells embedded in the collagen gel or gels, and the evaluation step may further include a reagent extraction step of extracting the reagent after the staining step.

The staining step may include a live cell staining step of selectively staining live cells in the collagen gel or gels.

The culture solution may be a serum-free culture solution.

The animal cells which are cultured in the culture step may be primary cells.

The primary cells may be obtained from a slight amount, 0.001 to 1 g, of tissue.

(Cell dispersion step):

The animal cell-containing culture sample is usually a section of an organ or tissue separated from a living body. Such a cell obtained from living body tissue is called a primary cell and used for primary culture. A typical example of the primary cell is a tumor cell. Of the tumor cells, particularly a malignant tumor cell, that is, a cancer cell is an object of the anticancer agent sensitive test. A culture sample most preferably consists of cancer cells to be cultured, but in addition to the cancer cells it usually contains normal cells such as fibroblasts as a portion of living body tissue, and the like. Furthermore, it often occurs that dead cells, in addition to live cells, are contained as cancer cells.

The culture sample may beforehand be subjected to a dispersion process in which living body tissue is minced and dispersed into a liquid, or to a separation process in which cells other than cancer cells of interest and other substances which may interfere with the test are removed. The living body tissue which is used in the above-mentioned dispersion or separation process may be a slight amount, 0.001 to 1 g, of tissue. The primary cells are separated from living body tissue by the dispersion or separation process.

The specific means and conditions for the dispersion and separation processes may be the same as in conventional cell culture methods. Also, a cancer cell-containing culture sample may be cultured by the culture method of the present invention after preliminary culture by various culture methods to increase the number of the cancer cells of interest. For this preliminary culture there may be employed conventional culture methods such as monolayer culture, coated dish culture, on-collagen-gel culture, and the like. The culture method of the present invention may be applied not only to primary culture, but also to culture-tests (tests using cell culture) of subcultured cells. In the case where the culture-tests of subcultured cells are carried out, a sample containing subcultured cancer cells is used. In the preliminary culture, one method which is already known for culturing cells by adhering them to a support surface is a so-called monolayer culture method. Specifically, for example, a culture sample and a culture solution are placed in a culture container and kept under prescribed conditions, whereby only specific live cells containing cancer cells are proliferated under conditions where they are adhered onto a surface of a support such as the culture container. Apparatuses used and treatment conditions are those as in the conventional monolayer culture method. The material of the support surface on which the cells are adhered and proliferated may be selected so as to allow the cells to favorably adhere and proliferate, or the support surface may be coated with a chemical substance, a so-called cell adhesion factor, which allows the cells to favorably adhere and proliferate. As examples of the cell adhesion factors there can be cited various types of so-called extracellular matrices such as collagen, fibronectin, laminin and vitronectin. Of them, Type-IV collagen is preferred.

After culturing, unnecessary components of the culture which do not which do not adhere to the surface of the support, are removed by removing the culture solution from the culture container, whereby only live cells which are adhered to the surface of the support can be collected. Specifically, dead tumor cells, lumps of dead tumor cells, lumps of fibroblasts, substances not digested by enzymes, and the like can be removed. A means such as EGTA-trypsin treatment may be used for the collection of the live cells which are adhered to the support surface.

In the preliminary culture, in the case where the on-collagen-gel culture is carried out, a collagen gel layer can be used. The material for the collagen gel layer for the preliminary culture may be the same as the collagen material used to form a globular collagen gel as described later. The thickness of the collagen gel layer may be such that cancer cells do not directly adhere to a surface of the support. Cancer cells which are adhered to a surface of the collagen gel layer can easily be separated and collected from the support surface by treatment with collagenase.

As mentioned above, if the culture sample containing cancer cells is precultured on a surface of another support, even though the total amount of cancer cells initially obtained from living bodies and the like is small, the cancer cells can be embedded in the globular collagen gel to a suitable and sufficient density, allowing more tests to be conducted and providing greater accuracy of the tests. In addition, if a collagen gel layer is pre-formed on a support surface, if a culture sample containing cancer cells is cultured on a surface of the collagen gel layer, and if only live cells which are adhered to the surface of the collagen gel layer are collected by treatment with collagenase, the cancer cells proliferates on the collagen gel better than when they are cultured under directly adhered conditions to the support surface. The collagenase treatment for collecting the proliferated live cells rarely damages the live cells. This is because the collagenase treatment enzymolyzes the collagen gel layer itself onto which the live cells are adhered prior to affecting the live cells, and thus there is little adverse effect on the live cells.

If dextran sulfate is added to the culture solution to bring into contact with the globular collagen gel, dextran sulfate serves to prevent the collagen gel from contracting, because dextran sulfate suppresses the proliferation of fibroblasts. The proportion of dextran sulfate to add to the culture solution is preferably in a range of 5 to 100 µg per milliliter of the culture solution. The same effect is also produced when a serum-free culture solution is used instead of adding dextran sulfate to the culture solution.

(Embedding step):

A collagen solution used for forming the globular collagen gel(s) may contain a common collagen material conventionally used in various animal cell-embedded culture methods, a high-molecular material such as polysaccharides and other extracellular matrices, and a liquid material. For example, the collagen used is preferably acid-soluble type-I collagen. Various components other than collagen, which are necessary for culture, may also be added to the collagen solution. The collagen solution preferably has the composition of a buffer solution to match with or approximate to physiological conditions of cancer cells of interest. As to animal-oriented cancer cells, the solution is buffered to a pH of 6.2 to 7.6, preferably 6.8 to 7.4, while the ionic strength is preferably set within a range of 100 to 180 mmols, preferably 140 to 160 mmols in NaCl concentration. Conventional methods may be applied for mixing the culture sample into the collagen solution. The density of cancer cells to seed into the collagen solution is preferably in a range of about $10^3$ to about $10^7$ cells/ml. Especially for the primary culture, the density is preferably in a range of about $10^4$ to about $10^7$ cells/ml.

The collagen concentration and the viscosity of the collagen solution influences the structure of the later-mentioned globular collagen gel. The specific quantitative conditions vary dependently on conditions such as the purpose of the test, but the collagen concentration is preferably in a range of 0.1 to 2.0 wt. %. In the case where the concentration is too high, the viscosity as mentioned below is high. On the other hand, in the case where the concentration is too low, the globular shape is difficult to maintain. The viscosity is preferably in a range of 50 to 2,000 centipoise, and more preferably 100 to 1,000 centipoise. In the case where the viscosity is too low, the cells precipitate in the collagen solution, comes into contact with a surface of the support, and proliferate in the form of a monolayer, thus making it impossible to make an accurate evaluation of effects of anticancer agents. On the other hand, the viscosity is too high, the collagen solution is difficult to handle. In addition, the gel strength upon gelation of the collagen solution also affects the performance, and therefore collagen used preferably has a gel strength of about 50 to about 1,000 g, more preferably about 50 to about 700 g, and still more preferably 100 to 500 g. The value of the gel strength is that which is measured according to JIS (Japanese Industrial Standard). In the case where the gel strength is too low, the globular collagen gel peels off from a surface of the support during tests, or the gel tends to contract. On the other hand, the gel strength is too high, the proliferation of cancer cells is inhibited.

The material and the structure of the support are not limited so long as it has a surface capable of fixing a collagen gel to it. For example, culture dishes such as Petri dishes and multidishes, flasks, and other conventional culture containers may be used as the support. In addition, culture plates such as glass or plastic cover slips and cell disks may also be used. The surface of the support is usually smooth and flat, but lines including frame-forming ridges and grooves to control the spread of the placed drop of the collagen solution may also be formed on the support surface. It is preferable that the above-mentioned culture containers and supports are optically transparent.

If a drop or drops of the collagen solution containing a dispersed culture sample is placed on a surface of the support, the surface tension of the collagen solution acts to form a water-like droplet or droplets on the surface of the support. As a result, a globular collagen gel or gels with a spherical convex surface can be formed. The shape of the globular collagen gel differs depending on factors such as the viscosity and temperature of the drop of the collagen solution which is placed, the amount of each drop of the collagen solution which is placed, the wettability of the support surface, and other conditions. In addition, it is preferable to set the gel to the desired shape depending on the test method to be employed including, for example, photography conditions when photographing the globular collagen gel for the image analysis.

As to how to place the globular collagen gel on the support, one or more drops of one collagen gel may be placed, or each drop of two or more collagen gels may be placed. In addition, when two or more collagen gels are cultured simultaneously, the gels may be in contact with each other on their partial or entire interface.

If the globular collagen gel with a convex surface is used, the globular collagen gel has a much smaller volume than a layered collagen gel, and thus, even when only a small amount of cancer cells is obtained from living body tissue, the cells can be seeded to a suitable and sufficient density. In addition, a wide area of the convex surface comes into contact with the culture solution, thus allowing for very efficient uptake of nutrients by the cells and excretion of waste from the cells. Furthermore if the size of the culture container is selected, the amount of the solution which comes into contact with the collagen gel can relatively be increased. The culture method of the present invention far more greatly improves the proliferativity of cells than conventional methods in which a collagen gel layer is formed over the entire internal bottom of a culture dish and nutrient and waste are exchanged only at a flat surface of the collagen gel layer.

In addition, the globular collagen gel is firmly fixed onto a support surface, because the globular collagen gel is formed by placing a drop or drops of a collagen solution containing cancer cells onto the surface of a support such as a culture dish, and then gelating the drop(s). Consequently, results of culturing cancer cells of interest may be observed or photographed while more easily specifying positions of the cells after culturing than results obtained by culturing cancer cells in a layered collagen gel. In addition, the method for placing a drop or drops of the collagen solution, for example, may include dropping the collagen solution from above the support surface, or gently placing the collagen solution into the form of a globular water-like droplet or droplets using a pipette near the support surface.

Specifically, under normal test conditions, the size of each globular collagen gel is made to be in a range of 3 to 300 microliters, and preferably 3 to 150 microliters, in terms of the volume of a drop of the placed collagen solution. For practical use, a range of 5 to 100 microliters is preferred, and a range of about 15 to about 50 microliters is more preferred. If primary cells are cultured, the gel is preferably about 30 microliters; and when using an established cell line, a gel of about 20 microliters is preferred. In addition, the height of the globular collagen gel is preferably made to be about 2 mm or less. The number of the formed collagen gel globules and their placement spacings on the surface of the support may optionally be varied as desired to match the measurements of the globular collagen gel and the structure of the support.

Conventional collagen gels used for microscopic observation and image analysis need to have a high transparency, but in the method according to the present invention even collagen gels with a relatively low transparency can be used. Specifically, collagen gels with a transmittance of 1 to 95% for 400 nm light can be used. A test even using collagen gels with a low transmittance within the above-mentioned range can satisfactorily be carried out without being affected by turbidity if the collagen gels are subjected to the later-mentioned stain treatment.

Samples which are mixed into the globular collagen gel are various cells, such as cancer cells and normal cells, and compounds which act on the cells, for example, calcium, inorganic salts such as calcium phosphate, lipids, carbohydrates, proteins.

(Culture step):

The formed globular collagen gel needs to be kept in a gel state at least until the culture finishes. Even a three-dimensional globular collagen gel becomes flat and dry if it loses moisture due to drying,. Once it is dried, it is difficult to restore to its original three-dimensional shape even if it is brought into contact with water. Thus the globular collagen gel is preserved, after its formation until the culture solution and the like are supplied, so that it may not excessively dry. So long as the globular collagen gel is in contact with the culture solution, there is no possibility that the gel may dry. After the completion of the culture, the fixing and drying of the globular collagen gel presents no problem for evaluating culture results.

If the support is a culture container such as a culture dish, the culture solution may be brought into contact with a surface of the support by simply pouring the culture solution into the container to cover the surface of the support. If the support is a culture plate, the culture solution may be poured in under conditions where the culture plate is placed in another culture container.

Various conventional culture solutions may be used depending upon test conditions. The composition of the culture solution is preferably suited for proliferating cancer cells of interest, but suppressing the proliferation of other cells. As culture solutions there are known serum culture solutions, which contain serum, and serum-free culture solutions, which are free from serum, and either may be used in the present invention. Serum-free culture solutions are characterized by containing no serum, unlike conventional culture solutions used for cell culture contain serum as one of their components. Consequently, the serum-free culture solution is prepared by combining various chemical substances necessary for culturing, except serum. The specific components and their proportions may be determined as needed, but serum-free culture solutions to be used have a composition which allows satisfactory proliferation of cancer cells of interest while suppressing the proliferation of other cells. Particularly a serum-free culture solution containing components which suppress the proliferation of fibroblasts is preferred. The serum culture solution, which is used, normally has a serum concentration of about 0.001 to about 5.0%, but good results are sometimes obtained even by using one with a serum concentration of about 5 to about 20%. Dextran sulfate can be added to the culture solution whether it contains serum or not. The amount of the culture solution is enough to cover the globular collagen gel for a satisfactory degree of culturing. In the case where the number of cancer cells as embedded in the globular collagen gel is large, the amount of the culture solution needs to be increased or the intervals of exchanging the culture solution during the culture needs to be shortened.

In the case where interactions of cells are observed in co-culture-tests and the like, a collagen layer which contains tested cells instead of the culture solution may be placed in the layered form over the entire container.

The culture is performed by keeping the culture solution in contact with the globular collagen gel as fixed to the support surface, for a prescribed period of time under environment conditions such as in a thermostat incubator or a carbon dioxide incubator. In order to test the sensitivity to an anticancer agent, it may be brought into contact with the globular collagen gel as fixed to the support surface, at an appropriate stage before or during the culture. Specifically, the anticancer agent may be added to the culture solution, or the culture solution may be exchanged with a culture solution to which the anticancer agent is added. Procedures and conditions for bringing the anticancer agent into contact with the collagen gel may be optional. In order to test effects of agents other than the anticancer agent, such agents may be brought into contact with the collagen gel in the same manner as the anticancer agent. When effects of a change of temperature, for example, by heating, or effects of radiations or the like are tested, the globular collagen gel may be exposed under those conditions for a given period of time.

(Evaluation step):

Depending on culture conditions, cancer cells in the globular collagen gel are proliferated or dead after the completion of the culture. Means of evaluation as in conventional culture methods may be applied in order to evaluate culture results, such as the proliferation state of cancer cells of interest. For example, the number of the formed colonies or cells may be counted by visual observation using a microscope, or an image obtained by photographing or imaging may be analyzed. Various characteristics of cancer cells may be observed and evaluated while the cancer cells are present in the globular collagen gel as fixed to a support surface.

When image analysis is carried out as a method for evaluating culture results, the placement form of the globular collagen gel on the support surface or the structure of the culture container or the like is set so as to facilitate the photographing and image analysis. Preferably a support with the aforementioned lines including ridges and grooves to restrict the shape is used in order to precisely set the shape and position of the globular collagen gel on a surface of the support. Images of cancer cells of interest and their colonies can be distinguished from other images such as of fibroblasts by utilizing image analysis in which photographed images are electronically processed and analyzed using a computer or the like, thus the proliferation state of the cancer cells of interest can accurately be evaluated, because cells as cultured under embedded conditions in the globular collagen gel show in-vivo-like proliferation morphology.

After culturing using the globular collagen gel, if only live cells in the globular collagen gel are selectively stained and if its results are evaluated, then live cancer cells can accurately be distinguished from dead ones, thus allowing an accurate evaluation of the proliferation state of cancer cells being studied in the culture-test. The stain method may be a conventional method for staining various cells, so long as it is a method capable of selectively staining live cells as distinct from other substances including dead cells. Particular staining agents and staining conditions may be according to conventional methods. For example, NR (neutral red) stain methods or latex particle stain methods in which phagocytic activity of cells is utilized, FDA (fluorescein diacetate) stain methods in which enzyme activity in cells is utilized, or other stain methods using a fluorescent reagent, or the like may be used.

An example of the treatment for selectively staining only live cells is an NR stain treatment, which uses NR stain as the staining agent. Stain conditions may be the same as in conventional NR stain. In this NR treatment, if a pigment is fixed into cells and if the globular collagen gel is then dried, the dried globular collagen gel reflecting culture results by the stained state can be preserved for a long time, and the procedure of evaluation such as by image analysis provide the same accurate analysis whenever the evaluation procedure may be made. NR stain is a preferable method for selectively staining only live ones of cancer cells, but if left to stand after staining, an NR-staining agent as incorporated into live cells elutes within a short period, thus making an evaluation impossible except just after staining. If then, as mentioned above, the pigment is fixed into cells by formalin fixation or the like, it becomes possible to temporarily prevent elution of the staining agent. If the globular collagen gel is then washed with water and dried, there is no possibility of degeneration or degradation. Means for drying, for example, may be water-absorption using filter paper, air-drying, or forcible drying by heating to a range of about 10° to about 50° C. The dried collagen gel prepared by removing the moisture from the globular collagen gel has a flat, sheet-like structure. The dried globular collagen gel can successfully be sealed using sealants such as Crystal/Maunt (product of Biomeda Corp.).

In addition, in the case where image analysis is performed, the photography procedure is much easier by setting the focus on cancer cells in a flat, dry collagen gel rather than on cancer cells in a three-dimensional, globular collagen gel, allowing a more focused image and thus a more accurate evaluation of culture results.

An FDA stain treatment is another treatment for selectively staining only live cells. This treatment is a method including measuring fluorescent coloring as produced by a reaction of an FDA staining agent upon live cells followed by exposure to excitatory light. Basic apparatuses and conditions for tests may be the same as in conventional FDA stain methods, but in the present invention the irradiation amount of excitatory light and the measurement environment temperature are set to within the ranges given later. The in-vivo-like morphology of colonies that fluorescently colored cells form in the globular collagen gel can be quantified and evaluated by image analysis. The FDA stain method is a method which allows satisfactory selective stain of only live ones of cancer cells. However, since conventional FDA stain methods include irradiating relatively strong excitatory light or carrying out the measurement at about normal temperature, these methods have disadvantages, for example, in that the activity of cancer cells is lowered. However, such disadvantages may be reduced if the irradiation amount and the temperature conditions are kept within the ranges given below. This makes it possible to evaluate the culture state by an FDA stain method prior to culturing cancer cells or at any stage during the culture, and to continue the culture thereafter. In other words, continuous evaluation of the culture state becomes possible. In particular, if the culture method under embedded conditions in the globular collagen gel is combined with the evaluation method utilizing image analysis, a highly precise measurement and evaluation can be made even under conditions where the irradiation amount of excitatory light is small and where the fluorescent coloring is weak, thus such a combined method is preferred.

Conditions for measurement after the FDA stain are as follows: the irradiation amount of excitatory light is in a range of $1 \times 10^0$ to $1 \times 10^7$ lux.sec, preferably $1 \times 10^1$ to $1 \times 10^5$ lux.sec, and the measurement environment temperature in a range of 1° to 15° C., preferably 8° to 12° C.

If colorimetric analysis as another method for evaluating culture results is carried out using a coloring reagent which selectively causes a color reaction due to metabolic activity of live cells as embedded in the globular collagen gel, then culture results can comparatively easily be evaluated even without using complicated equipments such as image analyzers. The accuracy of the evaluation is sufficient in practical application, particularly if a culture sample with little contamination by fibroblasts, or an established cell line, is used as a culture sample or if the contamination or proliferation of the fibroblasts is suppressed in any of the various manners as mentioned above. In addition, if the coloring agent is soluble in water, continuous evaluation can be made, because the water-soluble coloring agent gives no more affection to cancer cells than the FDA stain.

Specific methods and conditions for the step including the above mentioned colorimetric analysis may be the same as in culture-tests for other cells. The coloring reagent used may be an AB coloring reagent (trade name: Alamar Blue, product of Alamar Bioscience Co., Ltd.), a WST-1 coloring reagent, an XTT coloring reagent, an MTT pigment reductant, or the like.

A method, by which the measurement can be made even if cells are dead, is a method including selectively staining substances as contained in cells in the globular collagen gel, thus evaluating results. The stain methods employed may be a variety of conventional biochemical stain methods so long as they allow the selective stain of substances as contained in cells. Specific staining agents and conditions may be conventional ones, for example, staining reagents as used for staining tissue can be used. Practical examples of the staining agents are as follows: hematoxylin, Giemsa's solution, pigments such as Crystal Violet, ethidium bromide which stains nucleic acid, reagents which stain components such as proteins, carbohydrates and lipids, reagents which stain substances in cell membranes, reagents which stain specific parts such as cytoskeletons, antibodies against specific antigens, DNA probe, and the like.

If substances as contained in cells in the globular collagen gel are selectively stained and if its results are evaluated, the productivity of specific substances from cells can clearly be distinguished whether the cells are alive or not, thus the proliferation state of cancer cells which are objectives of culture-tests can accurately be evaluated from the substance productivity of the cells.

In addition, live cells or cell components can be stained doubly or triply. Various actions of cells can be evaluated for an identical sample by multiple stain of the cells.

Furthermore, the globular collagen gel may be separated from the support surface, for example, by dissolving the gel, thus evaluating culture results.

An example of the methods is a method including: quantitatively analyzing substances as contained in cells in the globular collagen gel; and evaluating its results. The quantitative-analysis methods employed may be a variety of conventional biochemical ones so long as they allow quantitative analysis of substances as contained in cells. Specific methods for quantitative analysis may be in accordance with conventional ones, for example, a commassie brilliant blue color method or Lowry method for quantitatively analyzing proteins, a DABA fluorescent coloring method for quantitatively analyzing nucleic acid, a luciferin luminescence method for measuring ATP, or various methods for quantitatively analyzing carbohydrates.

If substances as contained in cells in the globular collagen gel are quantitatively analyzed and if its results are evaluated, the productivity of specific substances from cells can clearly be distinguished whether the cells are alive or not, thus the proliferation state of cancer cells which are objectives of culture-tests can accurately be evaluated from the substance productivity of the cells.

In addition, another method includes quantitatively analyzing substances as secreted from cells in the globular collagen gel to a culture solution, and evaluating its results. The quantitative-analysis methods employed may be a variety of conventional biochemical ones so long as they allow quantitative analysis of substances as secreted from cells. Specific methods for quantitative analysis may be in accordance with conventional ones, for example, various methods such as methods for quantitatively analyzing lactic acid and the like which are typical metabolic products (waste).

If substances as contained in cells in the globular collagen gel are quantitatively analyzed and if its results are evaluated, the productivity of specific substances from cells can clearly be distinguished whether the cells are alive or not, thus the proliferation state of cancer cells which are objectives of culture-tests can accurately be evaluated from the substance productivity of the cells.

BEST MODE FOR CARRYING OUT THE INVENTION

Figure 1:
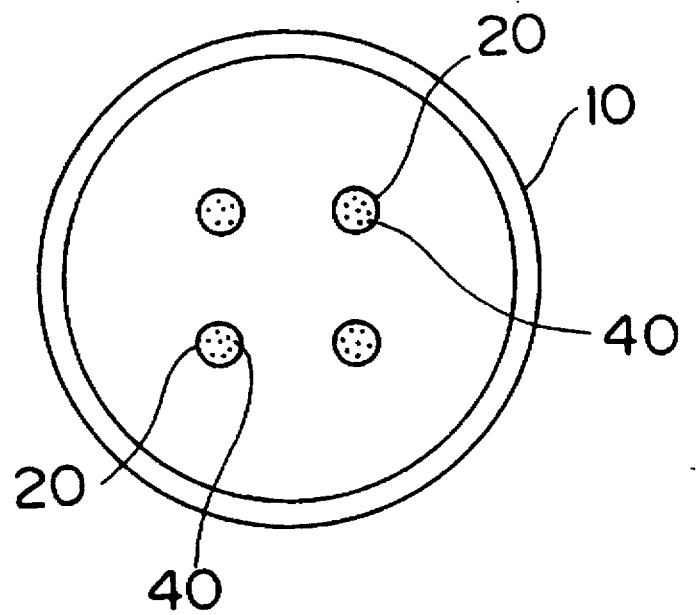
FIG. 1(a) is a plan view and an FIG. 1(b) is an enlarged sectional view showing a culture step using a globular collagen gel in an embodiment according to the present invention.
Figure 1:
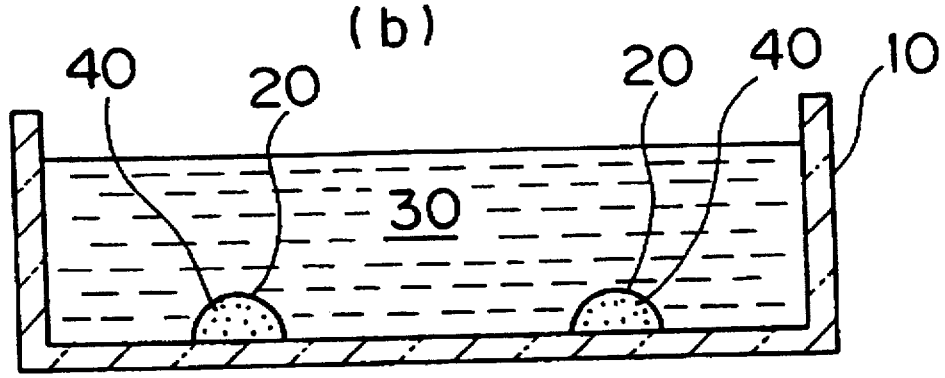

Hereinafter, the present invention is illustrated by the following examples of some preferred embodiments. However, the present invention is not limited to these examples.

An explanation will now be given regarding an anticancer agent sensitivity test as an example according to the present invention. A summary flow sheet is provided as Table 1.

TABLE 1

| Sensitivity Test Flow Sheet |
|---|
| (1) Starting materials (Surgical materials, biopsy samples, human cancer xenografts in nude mouse, established cell lines, etc.) |
| (2) Preliminary washing step |
| (3) Dispersion step (Cell dispersion/multienzyme complex) |
| (4) Separation step (Density gradient centrifugation) |
| (5) Preliminary culture (cell distinction) |

TABLE 1-continued

Sensitivity Test Flow Sheet (6) Preliminary proliferation culture (serum-free/serum proliferation culture solution)
(7) Cell re-dispersion step (treatment with collagenase alone)
(8) Culture under embedded conditions in globular collagen gel
(9) Agent contact (anticancer agent)
(10) Proliferation culture (serum-free/serum proliferation culture solution)
(11) Color reaction (cell viability measurement)
(12) Spectral analysis
(13) Stain (cell stain/coloring)
(14) Image analysis

EXAMPLE 1

Cancer cells were tested according to the collagen gel-embedded culture method of the present invention, in the order as shown in the flow sheet of Table 1, thus comparing effects of different anticancer agents.

(Starting materials):

Using a surgical sample as obtained from a human breast cancer patient as the starting material, it was treated according to the order as shown in the flow sheet.

(Dispersion step):

The capsule, fat, etc. were removed from the tissue containing the breast cancer using scissors and forceps under aseptic conditions, and then sliced with a razor. The sliced tissue was treated for two hours with a multienzyme complex containing collagenase (product of Nitta Gelatin Inc.), hyaluronidase (product of Chemical Co.), dispase (product of Godo Shusei Co., Ltd.), elastase (product of Wako Pure Chemical Industries, Ltd.) and DNase (product of Sigma Chemical Co.), thus digesting the interstitial tissue (see Example 1B).

(Separation step (principally blood cell separation)):

The tissue whose interstitial tissue had been digested in the previous step was filtered with a nylon mesh filter ($\phi$250 µm), the isolated cells were collected by centrifugal separation, and, then density gradient centrifugation was used to remove the blood-oriented cells, that is, blood cell components, and a portion of the fibroblasts (see Example 1C).

(Preliminary culture step (separation, purification, preliminary proliferation, and collection)):

The dispersion containing the cancer cells and the like as obtained in the preceding step (live tumor cell+fibroblasts+dead tumor cells+dead tumor cell lumps+substances undigested by enzymes) was plated onto a collagen gel (a collagen gel prepared on the bottom of a culture dish) for culture (for details see Example 1D). The culture solution at the time of the cell-seeding was DF culture solution+10% FBS (DF: a mixed culture solution containing one volume of Dulbecco's modified Eagle (DME) culture solution and one volume of Ham's F12 culture solution; FBS: fetal bovine serum) (see Example 1F).

Upon the preliminary culture of the dispersion containing the cancer cells and the like in the above-mentioned manner, it was observed that only the live cells adhered to the bottom of the culture dish and spread there. Specifically, upon observation with a microscope immediately after culturing and 24 hours thereafter, it was confirmed that the live cells had adhered to and had spread on the collagen gel, whereas the dead cancer cells, dead cancer cell lumps and substances undigested by the enzymes were suspended in without adhering to the collagen gel. The culture solution was then sucked from the culture dish, and the collagen gel on the bottom of the culture dish was washed. Observation with a microscope confirmed that the dead cancer cells, dead cancer cell lumps and substances undigested by the enzymes had been removed, leaving only the live cells adhered to and spread on the collagen gel.

The live cells, which were adhered to and spread on the collagen gel, were subjected to collagenase treatment for their separation, and the live tumor cells and the like were collected by centrifugal separation (see Example 1E).

In the preliminary culture as described above, basically the cells are separated and collected after 24 hours, but when there were few live tumor cells which were adhered to the collagen gel on the bottom of the culture dish, the preliminary culture time was extended (for example, to about 2–7 days), thereby allowing the live tumor cells to proliferate at the preliminary culture stage.

That is to say, even when the resulting live tumor cells were few, they were proliferated by the preliminary culture, thus making it possible to proceed to the next step.

(Embedding step):

The live tumor cells as obtained by the above-mentioned preliminary culture and collection steps were embedded into a globular collagen gel and cultured.

The embedded culture was carried out as follows: 1 volume of 10-fold concentrated Ham's F12 culture solution (sodium bicarbonate-free) and 1 volume of a reconstituting buffer solution (50 mM NaOH solution containing 260 mM sodium bicarbonate and 200 mM-HEPES) were added to 8 volumes of Cellmatrix Type I-A (0.3% acid-soluble Type-I collagen solution: product of Nitta Gelatin Inc.); the breast cancer cells and the like as obtained in the above-mentioned preliminary culture and collection steps were added and well mixed into the resultant mixture; the final concentration was adjusted to $5 \times 10^4$ cells/ml; and the resultant mixture was kept in ice.

Next, this collagen mixture solution was placed onto a 24-well multiplate at 30 µl/well using a micropipette and gelated to prepare globular collagen gels (for details see Example 1G).

According to this method, if a cell count of $5 \times 10^4$ is obtained after the preliminary culture, then the test may be conducted in 33 wells.

In contrast, using a conventional method (method described in Japanese Official Patent Provisional Publication (Kokai) No. Heisei 3-285696), 0.5 ml of the collagen mixture solution (cell density: $5 \times 10^4$ cells/ml) was needed per well and only 2 wells could be filled for testing.

(Agent contact step (using anticancer agents)):

A 0.5-ml portion of the culture solution containing an anticancer agent was superposed on the globular collagen gel in which the cancer cells were embedded and which was obtained in the above-mentioned embedding step, and the cancer cells were allowed to be in contacted with the anticancer agent by keeping them in a 5% carbon dioxide incubator at 37° C. for 24 hours. The following six anticancer agents were used: MMC (mitomycin C), CDDP (cisplatin), VDS (vindesine), VP-16, 5-FU (5fluorouracil) and ADM (adriamycin).

Then, the culture solution containing the anticancer agent was removed by suction, 0.5 ml of a culture solution free from an anticancer agent was instead added, the resultant mixture was shaken in a 5% carbon dioxide incubator, thus washing the globular collagen gel. This procedure was repeated at least every 10 minutes for a total of 3 times, whereby the anticancer agent was removed from the globular collagen gel.

(Culture step):

After the above-mentioned agent contact step, 0.5 ml of a culture solution was added, and the culture was effected at 37° C. in a 5% carbon dioxide incubator for 7–14 days. The culture solution was exchanged every 1–2 days. The proliferation culture solution as used was a culture solution containing a DF culture solution+10% FBS+5µg/ml insulin (product of Sigma Chemical Co.)+10 ng/ml EGF (EGF: epidermal growth factor, product of Becton Dickinson Labware)+20 ng/ml hydrocortisone (product of Sigma Chemical Co.) (see Example 1H).

(Colorimetric analysis step):

The viability of the cells in the sample as obtained by the culture was measured.

For the measurement, an AB coloring agent was used to cause a color reaction by the reductive activity of the cells.

The AB coloring agent was added in an amount of $\frac{1}{50}$–$\frac{1}{10}$ relative to the culture solution, and the reaction was conducted for 6 hours in a carbon dioxide incubator.

After the reaction, the culture solution was separated off, and the absorbance of the culture solution was measured using a spectrophotometer. The measurement of the absorbance was performed at 570 nm with a reference wavelength of 600 nm. The results are shown in Table 2.

TABLE 2

AlamarBlue Absorbance Measurement Results

| Anticancer agent | Control | MMC | CDDP | VDS | VP-16 | 5-FU | ADM |
|---|---|---|---|---|---|---|---|
| Absorbance | 0.95 | 0.40 | 0.40 | 0.69 | 0.87 | 0.69 | 0.65 |
| Effect/ control | 1.00 | 0.42 | 0.42 | 0.73 | 0.91 | 0.73 | 0.68 |

The same culture solution was also measured using a fluorospectrophotometer, with an excitatory wavelength of 560 nm and a detection wavelength of 590 nm. The results are shown in Table 3.

TABLE 3

AlamarBlue Fluorescence Measurement Results

| Anticancer agent | Control | MMC | CDDP | VDS | VP-16 | 5-FU | ADM |
|---|---|---|---|---|---|---|---|
| Fluorescence intensity ($10^2$) | 7.09 | 3.24 | 2.66 | 5.13 | 6.64 | 5.07 | 4.81 |
| Effect/ control | 1.00 | 0.46 | 0.38 | 0.72 | 0.94 | 0.71 | 0.68 |

(Fluorescent staining step):

The cultured cell sample as subjected to the colorimetric analysis was washed with a fresh culture solution, thus removing the coloring agent. The culture solution for the washing was free from sodium bicarbonate and cooled to 4° C. before use.

The culture container was then transferred to a cooled dark box. The culture solution was exchanged with a culture solution, to which an FDA-staining agent (FDA concentration: 2–10 µg/ml) which reacts due to esterase activity in live cells had been added, and was shaken for one hour in a refrigerator (10° C.), thus reacting the FDA with the cells.

The fluorescently colored cells were quantified by image analysis. The image for the image analysis was created using, an inverted fluorescent microscope, a sample holder cooling apparatus (in-house product), an excitatory light irradiation control apparatus, a sample holder driving apparatus and a high-sensitivity cooled CCD camera. The volume was measured on the basis of this image using an image analyzer according to a conventional method. The results are shown in Table 4. The intensity of the excitatory light was $1 \times 10^3$ lux.sec on the sample holder.

TABLE 4

FDA Volume Measurement Results

| Anticancer agent | Control | MMC | CDDP | VDS | VP-16 | 5-FU | ADM |
|---|---|---|---|---|---|---|---|
| Volume ($10^7$ µm$^3$) | 15.24 | 5.07 | 5.68 | 9.25 | 14.13 | 9.89 | 10.93 |
| Effect/ control | 1.00 | 0.33 | 0.37 | 0.61 | 0.93 | 0.65 | 0.72 |

In addition to the conventional known volume measurement by image analysis, the viability of the cells was also measured by quantifying the fluorescence intensity on the image. The results are shown in Table 5.

TABLE 5

FDA Image Fluorescence Measurement Results

| Anticancer agent | Control | MMC | CDDP | VDS | VP-16 | 5-FU | ADM |
|---|---|---|---|---|---|---|---|
| Fluorescence units ($10^1$) | 7.69 | 3.26 | 3.43 | 4.74 | 7.23 | 4.77 | 5.35 |
| Effect/ control | 1.00 | 0.42 | 0.45 | 0.62 | 0.94 | 0.62 | 0.70 |

(Spectrophotofluorimetry):

The cultured cell sample as subjected to the fluorescent stain was washed for one hour with a fresh cooled culture solution, thus removing the extracellular fluorescent reagent. The culture solution as used for the washing was a DME culture solution. This solution was further exchanged with a culture solution of 37° C., shaking was performed for one hour in an incubator at 37° C., and the FDA which had reacted in the cells was extracted into the solution. The culture solution was separated off and measured using a fluorospectrophotometer, with an excitatory wavelength of 490 nm and a detection wavelength of 520 nm. The results are shown in Table 6.

TABLE 6

FDA Spectrophotofluorimetry Results

| Anticancer agent | Control | MMC | CDDP | VDS | VP-16 | 5-FU | ADM |
|---|---|---|---|---|---|---|---|
| Fluorescence units ($10^1$) | 7.38 | 3.37 | 3.50 | 4.52 | 6.90 | 4.68 | 5.33 |
| Effect/ control | 1.00 | 0.46 | 0.47 | 0.61 | 0.93 | 0.63 | 0.72 |

(Pigment stain analysis step):

The cultured cell sample as subjected to the fluorescent analysis was washed with a fresh culture solution, thus removing the fluorescent reagent. The culture solution for the washing was a DME culture solution.

The culture solution was exchanged with a culture solution to which an NR-staining agent had been added (NR concentration: 25–50 µg/ml), and shaking was effected for 2 hours in a carbon dioxide incubator, thus incorporating the NR into the cells.

After the stain, the culture solution containing the NR was exchanged with PBS (Phosphate Buffered Saline), and the sample was allowed to stand stationary in a room for 10 minutes, thus removing the NR remaining outside of the cells.

Next, the PBS was exchanged with neutral 10% formalin, and the sample was allowed to stand stationary in a room for 40 minutes, thus fixing the cells and the NR as incorporated into the cells.

The globular collagen gel to which the cells had been fixed was immersed in distilled water for 10 minutes, thus removing the salts. When the globular collagen gel which had been immersed in the distilled water was air-dried at room temperature, whereby a flat dried product was formed.

At this time, the cultured cells were fixed in the dried collagen gel while containing the NR. These fixed cells exhibited no discoloration and endured long-term preservation.

The volume of the fixed cells was measured using an image analyzer in the same manner as mentioned above. The results are shown in Table 7.

TABLE 7

| Anticancer agent | Neutral Red Volume Measurement Results | | | | | | |
|---|---|---|---|---|---|---|---|
| | Control | MMC | CDDP | VDS | VP-16 | 5-FU | ADM |
| Volume ($10^7$ μm$^3$) | 16.90 | 5.19 | 6.25 | 10.10 | 15.54 | 10.76 | 12.26 |
| Effect/ control | 1.00 | 0.31 | 0.37 | 0.60 | 0.92 | 0.64 | 0.73 |

(Discussion):

From the results obtained in the above-mentioned steps, it was understood that the same results were obtained in a variety of cell measurement by combining the culture method using a globular collagen gel according to the present invention with the aforementioned high precision tissue/cell separation step and the like.

EXAMPLE 1A

It was experimentally confirmed that the test method of the present invention as described above (Method A) is more suitable for testing anticancer agent sensitivity of human cancer than conventional test methods.

The conventional test methods are as follows:

Method B: HTCA Method employing the soft agar method (method of Von Hoff and 9 others disclosed in "Cancer Research", Vol. 43; pp. 1926–1931, published in 1983);

Method C: Collagen gel culture method and measurement (method of Koezuka and 6 others disclosed in "Tissue Culture Research", Vol. 6, No.1, 1987);

Method D: Collagen gel culture method and image analysis (method of Koezuka and 4 others disclosed in Japanese Official Patent Provisional Publication (Kokai) No. Heisei 3-85696).

The test method according to the present invention was carried out as in Example 1, and the conventional test methods were carried out as described in the respective documents.

The anticancer agents used were, in addition to the 6 types used in Example 1, a few other anticancer agents, or combinations thereof, and the anticancer agent sensitivity was tested using 630 cases of human cancer as obtained by surgical removal.

The number of cases that could be tested for anticancer agent sensitivity using Method A was 597 of the 630 cases (success rate: 94.8%).

The number of cases that could be tested for anticancer agent sensitivity using Method B was 57 of the 630 cases (success rate: 9.04%).

The number of cases that could be tested for anticancer agent sensitivity using Method C was 219 of the 630 cases (success rate: 34.8%).

The number of cases that could be tested for anticancer agent sensitivity using Method D was 321 of the 630 cases (success rate: 50%).

By this it was confirmed that the test method of the present invention has a higher success rate than the conventional test methods.

EXAMPLE 1B (Enzyme treatment methods)

As the starting materials there were used interstitial tissue-rich breast cancer (sample A1), gastric cancer (sample A2), esophageal cancer (sample A3), pancreatic cancer (sample A4), skin cancer (sample A5), liver cancer (sample A6), renal cancer (sample A7), uterine cancer (sample A8), mucilaginous colon cancer (sample A9), interstitial tissue-scant lung cancer (sample B1) and ovarian cancer (sample B2).

The capsule, fat, etc. were removed from each of the starting materials using scissors and forceps under aseptic conditions, and then sliced with a razor. The sliced tissue was treated with a multienzyme complex or stepwise enzyme treatment for 2 hours, thus digesting the interstitial tissue. Herein, a multienzyme complex containing collagenase, hyaluronidase, dispase, elastase and DNase was used for samples A1–A9 (method A), and a multienzyme complex containing collagenase, hyaluronidase and DNase was used for samples B1–B2 (method B). As a result of varying the cell dispersion method (method A or B) depending on the different cancerous tissues, the cancerous tissues were digested in a short time, and tumor cells with a high cell viability were obtained.

In contrast, when the cancerous tissues were dispersed by stepwise enzyme treatment using collagenase and pronase (product of Kaken Pharmaceutical Co., Ltd.) in accordance with a conventional method (Japanese Official Patent Provisional Publication (Kokai) No. Heisei 3-285696), the interstitial tissue-rich breast cancer, gastric cancer, esophageal cancer, pancreatic cancer, etc. and mucilaginous colon cancer required a long time (about 24 hours) for the collagenase treatment, and in addition, the cell viability of the live tumor cells was deteriorated by the pronase treatment. Moreover, when different cancer cells were dispersed with simple collagenase treatment (method C), a multienzyme complex containing collagenase and pronase (method D) and a multienzyme complex containing collagenase, pronase and trypsin (method E). As a result, in method C a long enzyme treatment time (about 24 hours) was required and the digestion of the interstitial tissue was insufficient. In methods D and E the interstitial tissue was digested in about 2 hours, but the yield of live tumor cells was decreased.

Furthermore, the globular collagen gel-embedded method was applied in the very same manner as in Example 1 except for using samples as treated by the respective methods. As a result, the best results were obtained by using method A or B, while although results were also obtained with methods C–E, the performance was inferior when compared with the application of method A or B.

EXAMPLE 1C (Density gradient centrifugation)

In Example 1 given above, the interstitial tissue in the sample was digested by the step of dispersing the cancer cells, the resultant dispersion was filtered with a nylon mesh filter ($\phi$250 µm), the cancer cells and the like were collected from the filtrate by centrifugal separation, and the density gradient centrifugation was performed, which made it possible to remove the blood cell components and a portion of the fibroblasts. The density gradient centrifugation method included preparing a density gradient of Percoll (product of Pharmacia Co.), superposing the dispersion solution containing the cells and the like onto the top layer of the Percol, and subjecting it to centrifugation at 3,000 rpm for 10 minutes using a swing rotor-type centrifuge.

As a comparative example, low speed centrifugal separation (700 rpm, 1 minute) was performed after filtration with a nylon mesh filter, or density gradient centrifugation was performed without filtration. As a result, in the former centrifugal separation, the removal of the blood cell components and of a portion of the fibroblasts was insufficient. And in the latter centrifugal separation, aberrations occurred in the Percol density gradient because of contamination by substances undigested by the enzymes, such that removal of the blood cell components and of a portion of the fibroblasts was insufficient. Tests were tried by the same steps as in Example 1 except for changing the above-mentioned density gradient centrifugation step to the step as in the comparative example. As a result, the tests could be carried out, but the performance was inferior when compared with Example 1.

EXAMPLE 1D (Selection of extracellular matrix to be used in preliminary culture)

First, experimental confirmation was made for the selection of the extracellular matrix to be used for the preliminary culture, i.e., the material for the support surface to be in contact with the cancer cells during the preliminary culture, according to the present invention.

The extracellular matrices used were a bacterial plastic dish, a plastic culture dish, a type-I-IV collagen-coated plastic culture dish, a cell adhesion factor (fibronectin, laminin or vitronectin)-coated plastic dish and a type-I collagen gel plastic dish. For the experiment, 14 cases of human lung cancer and 12 cases of human breast cancer were used as controls, and cancer cells as obtained by enzymatic treatment were seeded onto various matrices to a cell density of 5×10⁴ cells/ml. They were then cultured for 24 hours in a 5% carbon dioxide incubator at 37° C., and the cell adhesion and the cell-spread were observed with a microscope. From the visual impressions, none of the used cancer cells was adhered or spread on the bacterial plastic dishes, but all were adhered and spread on the plastic culture dishes. The adhesion and the spread of the cells was even better on the plastic dishes as coated with collagen (types I-IV) and with the cell adhesion factors. The extracellular matrix with particularly excellent cell adhesion and cell-spread was the type-IV collagen-coated dish. However, in preliminary culture as extended for 3 days or more, stable proliferation occurred in all cases on the type-I collagen gel plastic dish, while on the type-IV collagen-coated dish, hypertrophy of the cytoplasm occurred in 2 of the 14 lung cancer cases and in 1 of the 12 breast cancer cases, and the cell proliferation was unstable.

When the tests were conducted only substituting each of the above materials for the extracellular matrix as used in the preliminary culture step in Example 1, the most favorable results were obtained by Example 1, but a certain degree of satisfactory performance was also displayed by the other materials.

From this it is clear that the commercially available plastic dishes for cell culture can be used as extracellular matrices for preliminary culture, and that particularly when coated with type-IV collagen or the like, the cell adhesion and the cell-spread are both improved. Furthermore, it would be understood that in the case where the culture is carried out for a long time, the most stable proliferation is obtained on type-I collagen gel.

EXAMPLE 1E (Method for cell collection after preliminary culture)

A test was made for methods for separating the cells which had adhered and spread on the bottom surface of the culture dish during the preliminary culture. The separation method was carried out utilizing the commonly employed treatment with 1 mM EGTA and 0.1% trypsin. The number of the cases in which the cells were separated within 5 minutes by the treatment with 1 mM EGTA and 0.1% trypsin were 8 of the 14 lung cancer cases and 7 of the 12 breast cancer cases. In addition, the number of the cases which needed 5 minutes or more for the separation were 6 of the 14 lung cancer cases and 5 of the 12 breast cancer cases. Next, the separated cells were collected by centrifugation and embedded into the collagen gel, the culture was carried out at 37° C. in a 5% carbon dioxide incubator for 10 days using a culture solution containing a DF culture solution+10 FBS+10 ng/ml EGF+5 µg/ml insulin+20 ng/ml hydrocortisone, and the cell proliferation degree was then observed by microscopy. As a result, the cases which needed 5 minutes or more for the cell separation had unsatisfactory cell proliferation degrees.

In contrast, in the method of culturing on the collagen gel, 30 minutes of treating the collagen gel with 0.1% collagenase resulted in dissolution of the collagen substrate as well as cell separation under the same conditions in all the cases. The separated cells were collected by centrifugal separation and cultured under the same culture conditions as in the previously mentioned method, and the cell proliferation degree was observed. As a result, all the cases exhibited stable proliferation in the collagen gel.

Thus, it is clear that in the cell collection method as carried out after preliminary culture, cells with a higher degree of proliferation activity are obtained by combining the culture on a collagen gel with the collagenase treatment than by combining monolayer culture (plastic dish, type-IV collagen-coated dish, etc.) with EGTA+trypsin treatment.

EXAMPLE 1F (Selection of culture solution for preliminary culture)

Conventional preliminary culture methods generally employ a culture solution containing fetal bovine serum and cell growth factor (for example, DF culture solution+10% FBS+insulin+EGF+hydrocortisone), but this culture solution has a drawback in that the proliferation of fibroblasts is predominant at the preliminary culture stage.

Thus, an investigation was made with regard to a serum-free culture solution (DF culture solution+5 µg/ml insulin+

10 ng/ml EGF+8 ng/ml sodium selenite+10 µg/ml transferrin+5 mg/ml BSA) (BSA: bovine serum albumin) and a serum culture solution containing dextran sulfate (DF culture solution+10% FBS+insulin+EGF+hydrocortisone 10 µg/ml dextran sulfate).

The experimental materials used were the 14 cases of human lung cancer and 12 cases of human breast cancer which had adhered to the bottom of the culture dishes in Example 1A above as controls, and the above-mentioned culture solutions (the serum-free culture solution and the dextran sulfate-containing serum culture solution) were used to culture cells for 7 days. Upon microscopic observation of the proliferation of the fibroblasts, it was found that in all cases of the cancer cells as used in the experiment, the proliferation of the fibroblasts had been partially suppressed, and that the cancer cells had proliferated preferentially. With regard to a serum-containing culture solution for comparison (DF culture solution+10% FBS+insulin+EGF+hydrocortisone), 4 of the 14 lung cancer cases and 9 of the 12 breast cancer cases exhibited preferential proliferation of the fibroblasts. In addition, separation and contraction of the collagen gel layer was observed in some of the cases which exhibited preferential proliferation of the fibroblasts.

EXAMPLE 1G (Globular collagen)

A test was performed with various sizes of the globular collagen gel in Example 1.

Drops of the collagen mixture solution as used in Example 1 were placed with a micropipette onto a 6-well multiplate, in respective amounts of 1, 2, 3, 4, 5, 7.5, 10, 20, 30, 40, 50, 100, 150, 200, 250, 300, 400 and 500 µl per well. As a result, the collagen mixture solution formed convex globules of the shape in a range of a hemisphere to a horizontally spread hemisphere, depending on the amount of the placed drop, on the surface of the multiplate. The planar shape of the globular collagen gel 20 are generally circular as shown in FIGS. 1(a) and (b), but the globular collagen gel actually formed various planar shapes such as ellipses or polygons depending on the amount of the placed drop of the collagen mixture solution. FIGS. 2(a) and (b) show a difference in shape of the globular collagen gel 20, in which FIG. 2(a) shows that the globular collagen gel 20 is almost the shape of a hemisphere in the case where the amount of a placed drop of the collagen mixture solution is relatively small, and FIG. 2(b) shows that the globular collagen gel 20 is the shape of a horizontally spread hemisphere in the case where the amount of a placed drop of the collagen mixture solution is large.

The formed globular collagen gel solution was allowed to stand stationary for 30 minutes in a 5% carbon dioxide incubator at 37° C., whereby the globular collagen gel containing the cancer cells was formed and fixed onto the surface of the plates. The culture solution was then superposed on the gel, and the culture was effected for 7–10 days in a 5% carbon dioxide incubator at 37° C.

In the case where the amount of the placed drop of the collagen solution was 3 µl or less in the above-mentioned procedure, problems occurred in that the formed globular collagen gel dried immediately, that the cell viability was lowered by changes in the osmotic pressure, and that the cancer cells could not be held in the collagen gel and the cancer cells spread from the bottom of the gel to the surface of the culture dish. Furthermore, problems on the precision of the analysis occurred, because the cell count in 3 µl of the collagen solution was 150 or less such that a low population was only provided for the analysis.

In addition, in the case where the amount of the placed drop of the collagen solution was 300 µl or more, a large number (15,000 or more) of cancer cells were necessary for embedding and the shape of the formed globular collagen gel was indefinite.

Consequently it is seen that the preferred size of the globular collagen gel under the above-mentioned conditions is in a range of 5 to 100 µl in terms of the amount of the placed drop of the collagen solution, and that the optimum size is about 30 µl.

Figure 3:
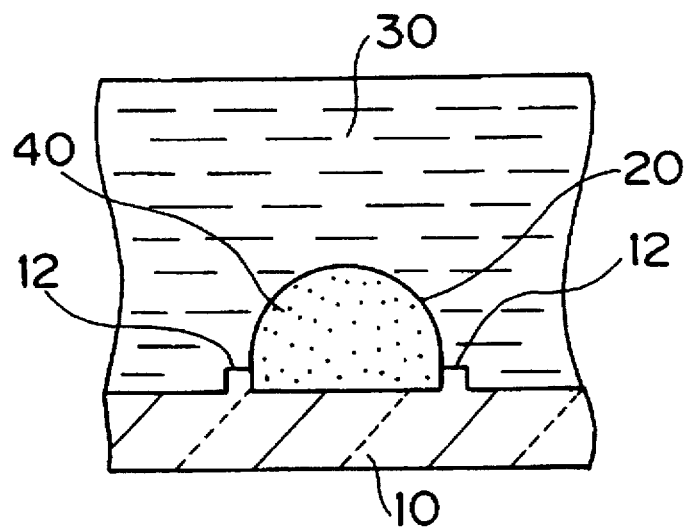
FIG. 3 is an enlarged sectional view showing a culture step in an embodiment according to the present invention.

Furthermore, a globular collagen gel was formed using a culture container with a lined structure as shown in FIG. 3. As seen in FIG. 3, lines to restrict the spread of the collagen solution are provided on the internal bottom face of a multiplate 10. Ridges 12 creating circular edges or the like are formed so as to match the outer periphery of the globular collagen gel 20 which is to be formed.

When using the lined culture container, the above-prepared collagen solution was poured so as to spread over the entire inside of the lines or ridges and to swell over the top thereof. This was then allowed to stand stationary for 30 minutes in a 5% carbon dioxide incubator at 37° C., thus preparing a collagen gel with a well-defined shape filling the lines. After the preparation of the collagen gel, the culture solution was superposed thereon and the culture was effected for 7–10 days in a 5% carbon dioxide incubator at 37° C. Also, the cells deeper than 2 mm from the gel surface in contact with the culture solution had less satisfactory proliferativity than those near the gel surface. That is to say, if the gel is thickened, the uniformity of proliferation of the cells is impaired or the precision of analysis is lowered.

Upon investigation of the relationship between the height of the globular collagen gel and its performance, it was found that in the case where the height of the globular collagen gel was 1.7 mm or greater under the conditions as in the above-mentioned example, the cell viability began to decrease, such that the proliferation lessened. In the case where the amount of the drop of the collagen solution was 50 µl, the height of the resultant globular collagen gel was 2.2 mm, such that poor proliferation was observed in the center of the gel. However, in the case where different types of cells were used or where the cell density was low, the proliferation was sufficient even if the height of the gel was 2.5 mm. In addition, the drop of the collagen solution was actually placed to prepare a globular collagen gel, surface tension effects made it difficult to prepare a globular collagen gel with a height of over 3 mm.

It was also confirmed that with a globular collagen gel with a thickness of 0.5 mm or less from the bottom of the culture dish, the globular collagen gel dried during the preparation of the gel, such that the cell viability was lowered, or the cells were not embedded in the globular collagen gel, such that monolayer proliferation occurred on the bottom of the culture dish. From this it was confirmed that in cases where the drop of the collagen solution is placed on a support surface with no lines, 3 to 300 µl of collagen solution is suitable for culturing cancer cells, and that in the case where the lined culture container is used, a collagen gel thickness of 0.3 to 3 mm is suitable for culturing cancer cells, with 1.7 mm being best.

In addition, the amount of the culture solution to be brought into contact with the globular collagen gel for culture is 2 times or more, usually 3 to times, preferably 10 to 50 times, more preferably 15 to 30 times, of the volume of the gel which ranges provided good results with regard to the proliferation. In this method, for example, in the case where 30 μl of a globular collagen gel (cell density: $5\times10^4$ cells/ml) was used, about 30 tests could be performed if $5\times10^4$ cells were obtained upon the preliminary culture. The anticancer agent as impregnated in the collagen gel was also easy to wash and remove in the agent contact step. In contrast, according to a conventional method (Japanese Official Patent Provisional Publication (Kokai) No. Heisei 3-285696), 0.5 ml of collagen mixture solution (cell density: $5\times10^4$ cells/ml) was required per well and only two tests could be performed, and in addition, the anticancer agent was extremely troublesome to wash and remove in the agent contact step, and the anticancer agent as impregnated in the collagen gel was not sufficiently washed and removed, wherein the amount of the culture solution was 0.5 to 2 times as large as the volume of the gel, and the proliferativity of the cells was poorer than when the globular collagen gel was used.

EXAMPLE 1H (Selection of proliferation culture solution used in culture step)

Figure 2A:
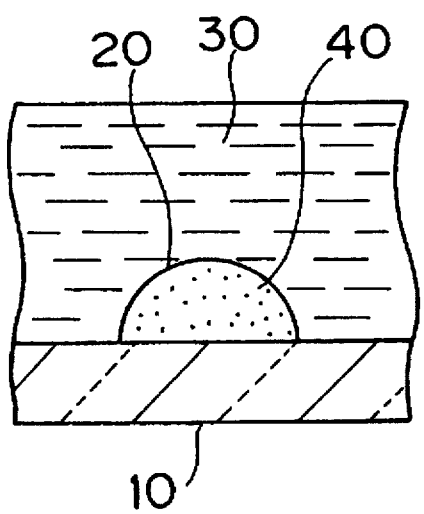
FIGS. 2(a) and (b) are sectional views showing examples of the shape of a globular collagen gel.
Figure 2B:
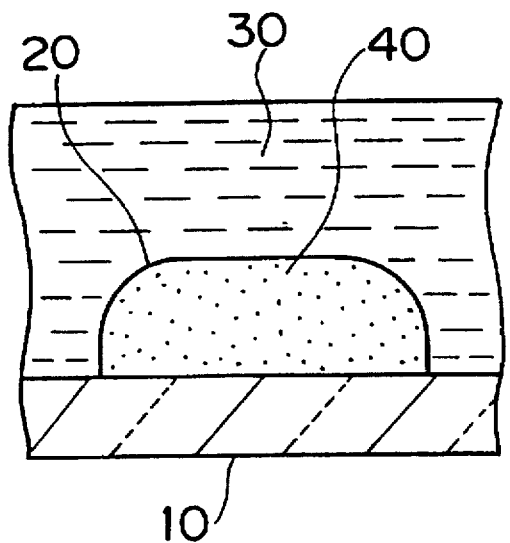

FIG. 1 shows an example of the culture step. Hemispherical globular collagen gel 20 are formed and fixed at 4 appropriately spaced locations on the internal bottom face of a flat circular multiplate 10. The cancer cells of interest 40 are embedded in the globular collagen gels 20. A culture solution 30 is poured into the multiplate 10, in a volume enough to cover the globular collagen gels 20 and to allow satisfactory proliferation of the cancer cells.

Favorable results were obtained upon comparison of all cases including when, as the proliferation culture solution in Example 1, there was used a culture solution containing DF culture solution+10% FBS+insulin+EGF+hydrocortisone for collagen gels with little contamination by fibroblasts; or a serum-free culture solution (DF culture solution+insulin+EGF+transferrin+hydrocortisone+sodium selenite+BSA) or a culture solution containing dextran sulfate (DF culture solution+10% FBS+insulin+EGF+hydrocortisone+sodium dextran sulfate) for collagen gels with much contamination by fibroblasts.

Thus, it was found effective to select the proliferation culture solution depending on the fibroblast contamination rate.

EXAMPLE 1I (Fibroblast contamination)

As the cell materials for the method as in Example 1 there were selected a human cancer-oriented cancer cell line (C cells) and a human-oriented fibroblast line (F cells), from established cell lines. Each step was carried out in the same manner as in Example 1, with the only difference that when the cells were embedded in the collagen gel, C cells and F cells were mixed with each other in appropriate proportions (1:0–1:4–1:10).

As a result of this culturing, globular proliferation formation of C cells and fibrous proliferation formation of F cells were observed with a microscope. The proliferation formation of F cells was remarkable as to the control group with which no agent was brought into contact. As to the agent-contacted groups there was seen a tendency toward agent concentration-dependent reduction in the proliferation of C and F cells.

Based on these observations, the results of colorimetric analysis by the aforementioned AB method were compared with those of volume measurement by image analysis using the aforementioned NR stain. As a result, a difference was found between the results of the analysis by the AB method and those of the NR stain image analysis, with regard to the evaluation of effects of the agents upon the cells. In addition, when analytical conditions of the image analyzer were changed from conventional ones, thus making analysis including volume analysis of the fibroblasts, the results agreed with effects of the agents as measured by the AB method.

Effects of the F cells upon the measured value of C cells in the control with which no anticancer agent was brought into contact are shown in Table 8, where AB denotes the absorbance as measured by the AB method, NR+F denotes the volume including F cells as measured by the NR method, and NR–F denotes the volume of the C cells alone as measured by the NR method.

TABLE 8

| Evaluation of Effects of Fibroblasts (F) upon Cancer Cells (C) | | | | | | | |
|---|---|---|---|---|---|---|---|
| Mixing ratio C:F | 1:0 | 1:1 | 1:2 | 1:4 | 1:6 | 1:8 | 1:10 |
| AB | 0.39 | 0.36 | 0.43 | 0.59 | 0.72 | 0.91 | 1.04 |
| NR + F ($10^7$ μm$^3$) | 3.14 | 4.36 | 4.22 | 6.22 | 7.35 | 9.65 | 11.08 |
| NR – F ($10^7$ μm$^3$) | 2.97 | 3.07 | 3.00 | 3.13 | 3.26 | 3.25 | 3.25 |

From the above it is clear that, as to samples as contaminated with fibroblasts, image analysis provides a more reliable analysis and is thus more preferable, when compared with the AB method.

In addition, when various surgical samples were used as the starting materials and when the test was conducted in the same manner as in Example 1, contamination by fibroblasts was observed as a result of culturing some of the samples. In these cases, as in the model test in which the above-mentioned, established cell lines were used, the values as measured for cancer cells suffered interference from fibroblast proliferation. Thus it would be understood that when a cell measure method with low selectivity, such as the AB method, is used, the sample should be adequately observed prior to measurement, thus taking the reliability of the measured values into consideration.

EXAMPLE 2

Materials surgically obtained from human cancer patients (gastric cancer, esophageal cancer, pancreatic cancer, skin cancer, liver cancer, renal cancer, uterine cancer) were used as samples for testing, and effects of anticancer agents were tested according to the procedures and method as in Example 1. However, the culture solution in the culture proliferation step was DF culture solution+10% FBS+insulin+EGF+hydrocortisone+sodium dextran sulfate.

As a result, satisfactory test results were obtained for all the samples. Consequently, the method according to the present invention can be applied to tests of surgical samples containing any type of cancer cell.

EXAMPLE 3

Effects of different anticancer agents were tested according to the same procedures as in Example 1 above, using as the starting material for the test a surgical sample (colon cancer) as obtained from a human cancer patient. The obtained colon cancer was thoroughly washed with a culture solution containing a high concentration of antibiotics (500 µg/ml kanamycin and 1 mg/ml penicillin), and then dispersion and separation steps were conducted according to the method as in Example 1. The resultant dispersion solution containing the cancer cells and the like (live tumor cells+fibroblasts+dead tumor cells+dead tumor cell lumps+substances undigested by enzymes) was plated on a type-IV collagen-coated culture dish or flask (hereinafter referred to as "type-IV collagen substrate"), thus culturing cells.

The culture solution at the time of the cell-seeding was DF culture solution+10% FBS. Next, 24 hours after the cell-seeding, the culture solution on the culture dish was sucked and the collagen coated bottom of the culture dish was washed, whereby the dead tumor cells, the dead tumor cell lumps and the substances undigested by the enzymes were removed. In addition, in order to suppress the proliferation of *Escherichia coli* and saprophytic bacteria as suspected of contaminating the culture system, washing was again performed with a culture solution containing a high concentration of antibiotics (500 µg/ml kanamycin and 1 mg/ml penicillin).

Next, the cells which had adhered and spread on the type-IV collagen substrate were separated therefrom using 1 mM EGTA at 37° or 4° C., and then using 0.1% trypsin (product of Difco Laboratories) at 37° C. or 0.03% trypsin (product of Sigma Chemical Co.) at 4° C., and the live tumor cells and the like were collected by centrifugal separation.

The steps as not mentioned above were carried out according to the same procedures and methods as in Example 1. However, in the proliferation culture step, there was used a culture solution containing a high concentration of antibiotics, which was a mixture of DF culture solution+10% FBS+insulin+EGF+hydrocortisone+500 µg/ml kanamycin+1 mg/ml penicillin.

As a result, it was confirmed that the anticancer agent sensitivity of the colon cancer could also be tested.

EXAMPLE 4

The same procedures and conditions as in Example 1 were used, except that the starting materials used were different surgical samples (lung cancer, ovarian cancer, thyroid gland cancer, brain tumor) as obtained from human cancer patients. However, in the dispersion step, interstitial tissue and the like of the sliced tissues were treated for 2 hours with a multienzyme complex containing collagenase, hyaluronidase and DNase, thereby digesting interstitial tissue in the sliced tissues.

The steps as not mentioned above were carried out according to the same procedures and methods as in Example 1. As a result, it was confirmed that the anticancer agent sensitivity of human lung cancer, ovarian cancer, thyroid gland cancer, and brain tumor could be tested.

EXAMPLE 5

Effects of different anticancer agents were tested according to the same procedures and methods as in Example 1 using as the starting materials cancer cell-containing ascites and pleural effusion as obtained from a human cancer patient. However, the dispersion step was omitted since it is unnecessary for ascites and pleural effusion. The preliminary culture step was omitted when not particularly necessary. As a result, it was confirmed that the anticancer agent sensitivity of the cancer cells as contained in the ascites and pleural effusion could be tested.

EXAMPLE 6

Effects of different anticancer agents were tested according to the same procedures and methods as in Example 1 using as the starting material lymph nodes containing metastatic cancer cells as obtained from a human cancer patient. As a result, it was confirmed that the anticancer agent sensitivity of the metastatic cancer cells could be tested.

EXAMPLE 7

Effects of different anticancer agents were tested according to the same procedures and methods as in Example 1 using as the starting materials biopsy samples as obtained from a human cancer patient.

The biopsy samples were obtained by medically used definite diagnosis, such as stab needle biopsy or endoscopy, or by cytodiagnosis, and suspended in a culture solution for tissue collection. Twenty biopsy samples having a solid content distribution of 0.001 to 1 g were used, among which 16 samples were 0.001 to 0.3 g heavy, and 10 samples were 0.001 to 0.1 g heavy, thus any sample was a fine tissue. The shapes of the respective tissues of the biopsy samples did not need any more to be cut into fine ones, because they had already been cut into fine ones in a medical manner. Cancer cells as already released from tissues and blood-oriented cells were also contained in the solution for tissue collection.

Depending on such characteristics of the starting materials, the dispersion step, the separation step and the preliminary culture step were modified as follows.

The biopsy samples were collected by centrifugal separation, some or all of the interstitial tissues were dispersed by dissolving them using collagenase, and only live cells were separated from them by density gradient centrifugation. Particularly in the density gradient centrifugation, the capacities of centrifugal tubes were changed to 2, 3, 4, 5, 10, 15, 30, and 60 ml, depending on the amount of the sample. In addition, the respective density gradients of proteins, such as Ficoll (product of Pharmacia Co.), albumin and gelatin, as well as Percoll were prepared to separate cells.

In the preliminary culture step, culture containers were selected from 5 types of multiplates with 96, 48, 24, 12, and 6 wells (culture area: 0.4, 1, 2, 4, and 10 $cm^2$ respectively), depending on the amount of the sample, thus preparing layered collagen gels.

As a result, it was confirmed that the anticancer agent sensitivity of the biopsy samples could be tested.

EXAMPLE 8

Effects of different anticancer agents were tested according to the same procedures and methods as in Example 1 using human cancer as obtained from human cancer xenografts in nude mouse. As a result, it was confirmed that the anticancer agent sensitivity of the human cancer xenografts in nude mouse could be tested.

EXAMPLE 9

Effects of different anticancer agents were tested according to the same procedures and methods as in Example 1 using a cultured cell line as the starting material. However, the steps of dispersion, separation, and preliminary culture were omitted, because they were unnecessary for the cultured cell line. As a result, it was confirmed that the anticancer agent sensitivity of the cultured cell line could be tested.

EXAMPLE 10

Effects of using endocrinotherapeutic agents instead of the anticancer agent were tested according to the same procedures and methods as in Example 1, except for the agent contact step and except that a surgical sample (breast cancer) as obtained from a human cancer patient was used as the starting material.

In the agent (endocrinotherapeutic agent) contact step, 0.5 ml of a culture solution containing representative endocrinotherapeutic agents, namely anti-hormone preparations (TAM: tamoxifen, MPA: medroxyprogesterone acetate), was superposed on the cancer cellcontaining globular collagen gel as obtained in the embedding step, and the agents were continuously brought into contact with the cells in a 5% carbon dioxide incubator at 37° C., thus carrying out culture. The subsequent procedures were carried out according to the same methods as in Example 1, thus testing effects of the anti-hormone preparations. As a result, it was confirmed that the sensitivity of the breast cancer to endocrinotherapeutic agents such as anti-hormone preparations could be tested.

EXAMPLE 11

Effects of using an immunotherapeutic agent instead of the anticancer agent were tested according to the same procedures and methods as in Example 1, except for the agent contact step and except that a surgical sample (breast cancer) as obtained from a human cancer patient was used as the starting material.

A 0.5-ml portion of a culture solution containing the immunotherapeutic agent TNF (Tumor Necrosis Factor) was superposed on the cancer cell-containing globular collagen gel as obtained in the embedding step, and the culture was effected in a 5% carbon dioxide incubator at 37° C. The subsequent procedures were carried out according to the same methods as in Example 1, thus testing effects of the TNF. As a result, it was confirmed that the immunotherapeutic agent sensitivity of the breast cancer could be tested.

EXAMPLE 12

Effects of carrying out a thermal treatment step instead of the anticancer agent contact step were tested according to the same procedures and methods as in Example 1, except for the thermal treatment step substituting for the agent contact step and except that a surgical sample (breast cancer) as obtained from a human cancer patient was used as the starting material.

In the thermal treatment step, 0.5 ml of the culture solution was superposed on the cancer cell-containing globular collagen gel as obtained in the embedding step, and then allowed to stand stationary for one hour in an incubator at 43° C., thus thermally treating the human cancer cells. After the thermal treatment, the cells were cultured in a 5% carbon dioxide incubator at 37° C. The subsequent procedures were carried out according to the same methods as in Example 1. As a result, it was confirmed that the sensitivity of the breast cancer to heating could be tested.

EXAMPLE 13

Effects of carrying out a radiation treatment step instead of the anticancer agent contact step were tested according to the same procedures and methods as in Example 1, except for the radiation treatment step substituting for the agent contact step and except that a surgical sample (breast cancer) as obtained from a human cancer patient was used as the starting material.

In the radiation treatment step, 0.5 ml of the culture solution was superposed on the cancer cell-containing globular collagen gel as obtained in the embedding step, and then irradiated with 10 Gy of Cobalt 60. After the radiation treatment, the cells were cultured in a 5% carbon dioxide incubator at 37° C. The subsequent procedures were carried out according to the same methods as in Example 1. As a result, it was confirmed that the sensitivity of the breast cancer to radiation could be tested.

EXAMPLE 14

A test was conducted in the same way as in Example 1, but the FDA reaction in the fluorescent staining step was carried out not at 10° C., but at 37° C. A surgical sample (breast cancer) as obtained from a human cancer patient was used as the starting material, and the steps other than the fluorescent staining step were according to the same procedures and methods as in Example 1.

As a result, effects of the FDA reaction with the cancer cells and effects of the elution of the FDA reaction product from the cells were obtained simultaneously. And it was also possible to test the anticancer agent sensitivity of the cancer cells simply by measurement using a fluorospectrophotometer, without image analysis.

EXAMPLE 15

A test was conducted in the same way as in Example 1, but an antibody against PCNA was used instead of the NR-staining agent in the pigment stain analysis step. in addition, a lined cover slip was used instead of the 24-well multiplate in the embedding step. A surgical sample (breast cancer) as obtained from a human cancer patient was used as the starting material, and the steps other than the steps of embedding and pigment stain analysis were according to the same procedures and methods as in Example 1.

In the embedding step, drops of the collagen solution in which the culture sample was dispersed was placed onto a surface as surrounded by lines of the lined cover slip, such that the globular collagen gel was formed without spreading outside of the lines. The cells as obtained by the culture step were fixed using a 10% formalin prior to the stain. The antibody stain was tested using the antibody against PCNA (mouse antibody against rat PCNA, product of Medac Gesellschaft tür Klinische Spezialpraparate mbh) and an antibody stain kit (Immunohistochemical staining kit, product of Biomeda Corp.), in which respective trace amounts of the antibody solution and the antibody stain reagent were brought into contact with the cultured cell sample only inside the lines, thereby allowing the cancer cell antigen to be stained. As a result, it was possible to test the anticancer agent sensitivity of the cancer cells on the basis of their antigen production.

EXAMPLE 16

(NR extraction method):

A test was conducted in the same way as in Example 1, but the image analysis of live cells as stained with the NR was not carried out, and the NR was instead extracted from the live cells, thus measuring the absorbance. A surgical sample (breast cancer) as obtained from a human cancer patient was used as the starting material, and the test was carried out according to the same procedures and methods as in Example 1, except for the procedures of the formalin-fixation, the drying and the image analysis in the pigment stain analysis step. The NR as incorporated into live cells was extracted by dissolving the collagen gel with collagenase in the culture container and then adding an NR extractant, and the absorbance of the resultant extract was measured. Results are shown in Table 9.

TABLE 9

Neutral Red Absorbance Measurement Results

| 5-FU concentration (Cmax = 1) | Control | 0.1 | 0.2 | 0.4 | 0.6 | 0.8 | 1.0 |
|---|---|---|---|---|---|---|---|
| Absorbance | 0.348 | 0.307 | 0.206 | 0.123 | 0.100 | 0.079 | 0.072 |
| Effect/control | 1.00 | 0.88 | 0.59 | 0.35 | 0.29 | 0.23 | 0.21 |

EXAMPLE 17

(MTT assay method):

A test was conducted in the same way as in Example 1, but an MTT reagent was substituted for the AB coloring agent in the colorimetric analysis step. A surgical sample (breast cancer) as obtained from a human cancer patient was used as the starting material, and the test was carried out according to the same procedures and methods as in Example 1, except for the procedures subsequent to the colorimetric analysis step. The formazane as deposited in live cells was extracted by dissolving the collagen gel with collagenase in the culture container and then adding a formazane extractant, and the absorbance of the resultant extract was measured, when the deposited fine crystal of formazane was held in the collagen gel, such that results were obtained with good accuracy. The results are shown in Table 10.

TABLE 10

Formazane Absorbance Measurement Results

| 5-FU concentration (Cmax = 1) | Control | 0.1 | 0.2 | 0.4 | 0.6 | 0.8 | 1.0 |
|---|---|---|---|---|---|---|---|
| Absorbance | 1.175 | 1.036 | 0.774 | 0.599 | 0.515 | 0.450 | 0.429 |
| Effect/control | 1.00 | 0.88 | 0.66 | 0.51 | 0.44 | 0.38 | 0.37 |

EXAMPLE 18

(Giemsa's stain method):

A test was conducted in the same way as in Example 1, but Giemsa's solution as used for tissue stain was substituted for the NR-staining agent in the pigment stain analysis step. A surgical sample (breast cancer) as obtained from a human cancer patient was used as the starting material, and the steps other than the pigment stain analysis step were according to the same procedures and methods as in Example 1. The Giemsa stain was carried out for cells as beforehand fixed using a neutral 10% formalin. The volume of the stained cells was measured using an image analyzer. As a result, it was possible to test the anticancer agent sensitivity of the breast cancer.

EXAMPLE 19

(DNA quantitative method):

A test was conducted in the same way as in Example 1, but a DNA fluorescent quantitative method was substituted for the pigment stain analysis step. A surgical sample (breast cancer) as obtained from a human cancer patient was used as the starting material, and the steps other than the pigment stain analysis step were according to the same procedures and methods as in Example 1. In the DNA quantitative method, a sample was prepared by dissolving the collagen gel with collagenase in the culture container and then collecting cells. However, in the case where the amount of the cells in the collagen gel was clearly unsatisfactory to the detection sensitivity in the DNA quantitative method, a needed number of collagen gels containing cells as brought into contact with the agent under the same conditions were collected before the cells were collected. The collected cells were fixed using ethanol, and fluorescence as emitted using a DABA reagent was measured using a fluorospectrophotometer. As a result, it was possible to test the anticancer agent sensitivity of the breast cancer.

EXAMPLE 20

(Multiple stain):

A test was conducted in the same way as in Example 1, but different staining agents were substituted for the NR-staining agent in the pigment stain analysis step. A surgical sample (breast cancer) as obtained from a human cancer patient was used as the starting material, and the steps other than the pigment stain analysis step were according to the same procedures and methods as in Example 1. For the multiple stain, Calcein and ethidium bromide were used. As to the stained cells, the volume of the live cells and that of the dead cells were severally measured with Calcein and ethidium bromide respectively, using an image analyzer. As a result, it was possible to test the anticancer agent sensitivity of the breast cancer.

EXAMPLE 21

(Substances produced from cells in culture solution):

In the culture step after the agent contact step as in Example, the used culture solution was daily exchanged with a new one and collected, such that lactic acid as contained in each of the collected culture solutions was quantitatively analyzed. A surgical sample (breast cancer) as obtained from a human cancer patient was used as the starting material to carry out a test according to the same procedures and methods as in Example 1, except that the used culture solutions were collected during the culture step in the above-mentioned way. The quantitative analysis of lactic acid was carried out using a reagent kit for food analysis (F-kit L-lactic acid, product of Boehringer Mannheim GmbH), and the absorbance was measured. As a result, it was possible to test the anticancer agent sensitivity of the breast cancer.

(Test using co-culture):

EXAMPLE 22

Two globular collagen gels were prepared in one culture container to culture different types of cells, of which the interactions were evaluated.

As to the cells, each one type of cell was selected from the following groups A and B and embedded into different globular collagen gels respectively.

Group A (group of fibroblasts-oriented cell lines):
  MRC-5, NB1-RGB
Group B (group of human cancer-oriented cell lines):
  QG-56, PC-3, C-1, PC-13, KATO-3, PC-14

The collagen gel solution for embedding cells was prepared by adding 1 volume of 10-fold concentrated Ham's F12 culture solution (sodium bicarbonate-free) and 1 volume of a reconstituting buffer solution (50 mM NaOH solution containing 260 mM sodium bicarbonate and 200 mM-HEPES) to 8 volumes of Cellmatrix Type I-A (0.3% acid-soluble Type-I collagen solution: product of Nitta Gelatin Inc.), and preserved in ice, such that the collagen solution separated into two liquids A and B. Then, the above-mentioned cell lines A and B were added and well mixed into two portions of the solution respectively to adjust their final cell density to $5 \times 10^4$ cells/ml, thus preparing collagen mixture solutions.

Figure 4:
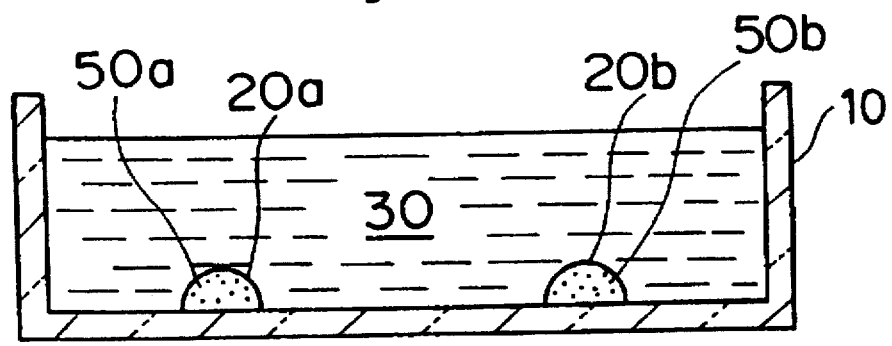
FIG. 4 is an enlarged sectional view showing a culture step in Example 22.

Each one drop of the resultant collagen mixture solutions was placed into the shape of a hemisphere in an amount of 30 μl per well at any one of two sites with an appropriate interval on a 6-well multiplate using a micropipette, thus forming and fixing hemispherical globular collagen gels 20a and 20b containing different types of cells as shown in FIG. 4. In FIG. 4, cells 50a of the group A are embedded in the globular collagen gel 20a, and cells 50b of the group B in the globular collagen gel 20b. A culture solution 30 was poured into the inside of the multiplate 10 in such a large amount that the solution 30 could cover the globular collagen gels 20a and 20b and allow live cells to sufficiently proliferate, particularly the amount of the poured culture solution 30 being 3 ml.

Under the conditions, the multiplate was preserved in a 5% carbon dioxide incubator at 37° C., thus carrying out co-culture.

In addition, as a comparative example, a globular collagen gel free from the cells of the group A was prepared, thus carrying out coculture in the same way as mentioned above.

Live cells of the cultured cells were stained using the Neutral Red, fixed, and dried, and then the volume of the cancer cell lines of the group B was calculated by image analysis.

As a result, variations were seen in the proliferativity of the cells of the group B, depending on combinations of cells of the groups A and B.

The variations are shown in Table 11 in terms of a ratio, (volume of group-B cells as co-cultured with group-A cells)/(volume of group-B cells in the comparative example).

TABLE 11

| | Effects of fibroblasts upon cancer cells | | | | | |
|---|---|---|---|---|---|---|
| Group B | QG-56 | PC-3 | C-1 | PC-13 | KATO-3 | PC-14 |
| Group A | | | | | | |
| MRC-5 | 4.0 | 1.8 | 1.6 | 1.4 | 0.9 | 0.3 |
| NB1-RCB | 1.6 | 1.1 | 0.9 | 1.2 | 1.0 | 1.1 |

EXAMPLE 23

Figure 5:
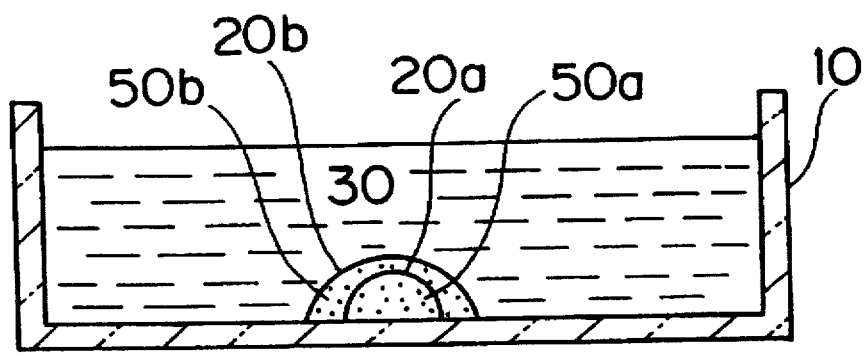
FIG. 5 is an enlarged sectional view showing a culture step in Example 23.

The procedure of Example 22 was repeated, but MRC5 was used as the cells of the group A, and QG-56 as the cells of the group B, and the following modifications were made. As shown in FIG. 5, a hemispherical globular collagen gel 20b was formed and fixed on the internal bottom of a flat circular multiplate 10. Next, a globular collagen gel 20a (100 μm) was placed so as to cover the globular collagen gel 20b with the globular collagen gel 20a. In FIG. 5, cells 50a of the group A are embedded in the globular collagen gel 20a, and cells 5b of the group B in the globular collagen gel 20b. In addition, the cell density at which the cells were contained in the globular collagen gel 20a was changed into a range of 0 to $5 \times 10^4$ cells/ml as the final density. A culture solution 30 was poured into the inside of the multiplate 10 in such a large amount that the solution 30 could cover the globular collagen gel 20b and allow live cells to sufficiently proliferate. The test was carried out in the same way as in Example 22 except for the number of the cells as contained in each globular collagen gel and for the placement of the gels.

As a result, the volume of QG56 varied with the variation of the density of MRC-5. Results are shown in Table 12.

TABLE 12

| Effects of MRC-5 upon QG-56 | | | | | |
|---|---|---|---|---|---|
| Density of MRC-5 ($1 \times 10^4$ cells/ml) | 0.0 | 0.5 | 1.0 | 2.5 | 5.0 |
| Volume of QG-56 ($10^7$ μm$^3$) | 2.1 | 3.4 | 5.8 | 8.3 | 9.1 |

EXAMPLE 24

Figure 6:
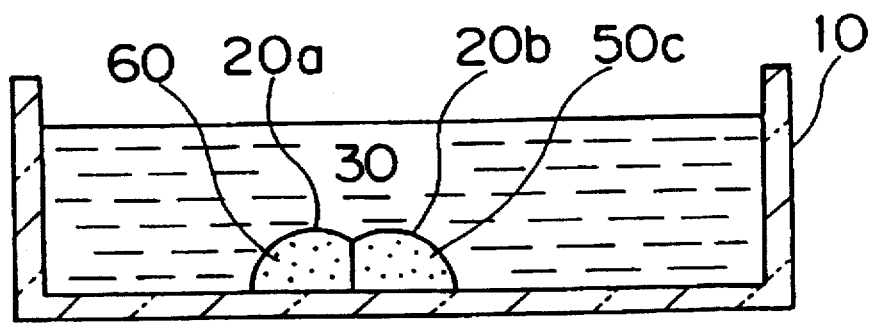
FIG. 6 is an enlarged sectional view showing a culture step in Example 24.

The procedure of Example 22 was repeated, but a calcium phosphate crystal was substituted for the cells of the group A, and rabbit bone marrow-oriented cells for the cells of the group B, and the following modifications were made. As shown in FIG. 6, hemispherical globular collagen gels 20a and 20b were formed and fixed on the internal bottom of a flat circular multiplate 10, such that the globular collagen gels 20a and 20b were in contact with each other on their vertical faces. In FIG. 6, the calcium phosphate crystal 60 are embedded in the globular collagen gel 20a, and the rabbit bone marrow-oriented cells 50c in the globular collagen gel 2b. A culture solution 30 was poured into the inside of the multiplate 10 in such a large amount that the solution 30 could cover the globular collagen gels 20a and 20b and allow live cells to sufficiently proliferate. The test was carried out in the same way as in Example 22 except for the components as contained in each globular collagen for the placement of the gels. In addition, the gel 20b was evaluated by microscopy.

As a comparative example, a globular collagen gel free from a calcium phosphate crystal was prepared as the gel 20a, thus carrying out culture in the same way as mentioned above.

As a result of Example, the calcification of extracellular matrices was remarkably observed with regard to cells as embedded in or near the interface where the gels 20a and 20b were in contact with each other. This observation was possible to easily carry out, because the interface was oriented in a vertical direction. However, as to the comparative example, the calcification in the interface was not observed.

EXAMPLE 25

Figure 7:
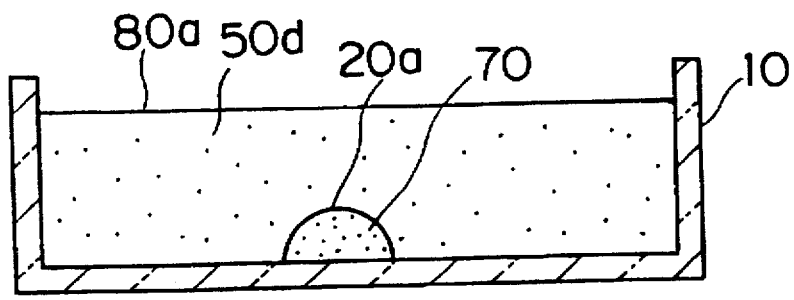
FIG. 7 is an enlarged sectional view showing a culture step in Example 25.

The procedure of Example 23 was repealed, but TGF-β (a transformation growth factor) was substituted for the cells of the group A, and rabbit-oriented vascular endothelial cells for the cells of the group B, and the following modifications were made. As shown in FIG. 7, a globular collagen gel 20d was formed and fixed on the internal bottom of a multiplate 10. In FIG. 7, the transformation growth factor 70 is contained in the globular collagen gel 20a. A collagen gel 80a in which the rabbit-oriented vascular endothelial cells 50d were embedded was placed in the layered form into the inside of the multiplate 10, such that the globular collagen gel 20a was covered with the collagen gel 80a. The test was carried out in the same way as in Example 22 except for the components as contained in each collagen gel and for the placement of the gels. In addition, the collagen gel 80a was evaluated by microscopy.

As a result, different proliferation shapes of the vascular endothelial cells were observed depending on the distance from the surface of the globular collagen gel 20a. Results are shown in Table 13.

TABLE 13

Effects of TGF-β upon vascular enothelial cells

| Distance (mm) from surface of gel 20a | 0 | 1 | 2 | 3 | 4 |
|---|---|---|---|---|---|
| Proliferation state of vascular endothelial cells | lump | tree | lump/ tree | lump | lump |

EXAMPLE 26

Figure 8:
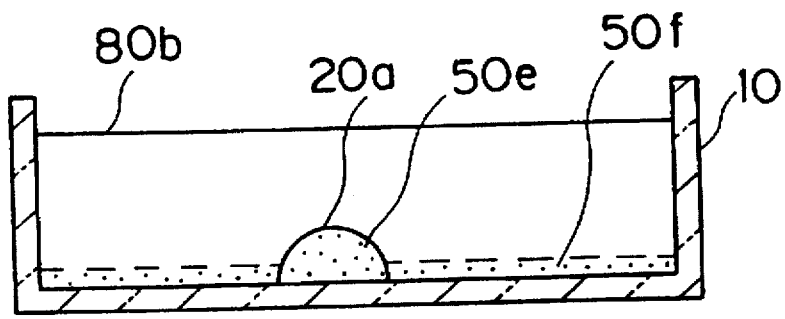
FIG. 8 is an enlarged sectional view showing a culture step in Example 26.

The procedure of Example 25 was repeated, but rat-oriented hepatic parenchymal cells were substituted for the cells of the group A, and rat fetus-oriented neuroblasts for the cells of the group B, and the following modifications were made. As shown in FIG. 8, a hemispherical globular collagen gel 20a was formed and fixed on the internal bottom of a multiplate 10. In FIG. 8, the rat-oriented hepatic parenchymal cells 50e are embedded in the globular collagen gel 20a, and the rat fetus-oriented neuroblasts 50f were directly coated on the internal bottom of the multiplate 10. A cell free collagen gel 80b was placed in the layered form on the rat fetus-oriented neuroblasts 50f in the inside of the multiplate 10, such that the globular collagen gel 20a was covered with the collagen gel 80b. The test was carried out in the same way as in Example 22 except for the components as contained in each collagen gel and for the placement of the gels in addition, the rat fetus-oriented neuroblasts 50f was evaluated by microscopy.

As a result, a variation in lengths of processes as elongated from the neuroblasts was observed depending on the distance from the surface of the globular collagen gel 20a. Results are shown in Table 4.

TABLE 14

Effects of hepatic parenchymal cells upon neuroblasts

| Distance (mm) from surface of gel 20a | 0 | 1 | 2 | 3 | 4 |
|---|---|---|---|---|---|
| Shape of neuroblasts | — | long | middle | short | short |

EXAMPLE 27

The procedure of Example 22 was repeated, but rabbit bone marrow-oriented cells were substituted for the cells of the group A, and 4 types of primary human lung cancer-oriented cells for the cells of the group B, and the following modifications were made.

Figure 9:
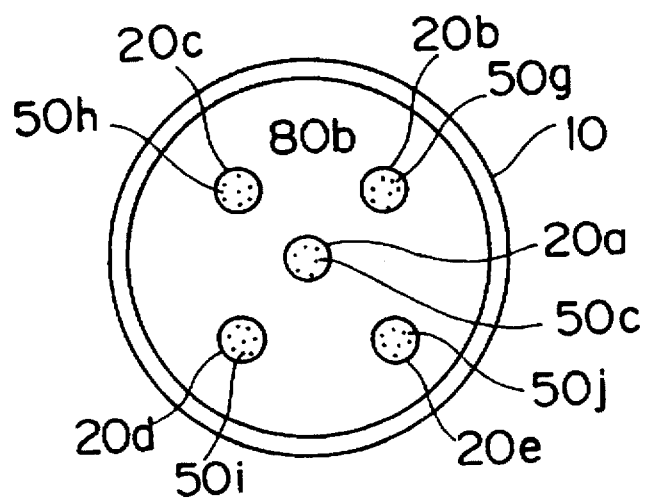
FIG. 9 is an enlarged sectional view showing a culture step in Example 27.

As shown in FIG. 9, a hemispherical globular collagen gel 20a was formed and fixed at the center of the internal bottom of a multiplate 10, and hemispherical globular collagen gels 20b, 20c, 20d and 20e containing different types of cells were formed and fixed at 4 sites with appropriate intervals around the globular collagen gel 20a. In FIG. 9, the rabbit bone marrow-oriented cells 50c are embedded in the globular collagen gel 20a, and the different types of lung cancer-oriented cells 50g, 50h, 50i and 50j are embedded in the globular collagen gels 20b, 20c, 20d and 20e respectively. A cell-free collagen gel 80b was placed in the layered form in the inside of the multiplate 10, such that the globular collagen gels 20a, 20b, 20c, 20d and 20e were covered with the collagen gel 80b. The test was carried out in the same way as in Example 22 except for the components as contained in the globular collagen gels and the layered collagen gel and for the placement of the gels.

As a comparative example, a globular collagen gel free from a cell was prepared as the globular collagen gel 20a, thus carrying out culture in the same way as mentioned above.

As a result, variations were seen in the proliferativity of the respective cells as embedded in the globular collagen gels 20b, 20c, 20d and 20e, depending on the cells as embedded in the globular collagen gel 20a. The variations are shown in Table 15 in terms of a ratio, (volume of lung cancer-oriented cells as co-cultured)/(volume of lung cancer-oriented cells in the comparative example).

TABLE 15

Effects of bone marrow-oriented cells upon cancer cells

| Globular collagen gel | 20b | 20c | 20d | 20e |
|---|---|---|---|---|
| Co-culture/ comparative example | 1.7 | 1 | 0.6 | 0.4 |

INDUSTRIAL APPLICATION

Even if the amount of animal cells is small, various tests for them can be carried out by the animal cell-embedded culture method according to the present invention, because this method includes the step of culturing the cells under conditions where they are embedded in a globular collagen gel. In addition, accurate tests are possible to carry out, because the proliferativity of animal cells during their culture by this method is very good. Furthermore, when culture results of the cells are evaluated, the evaluation utilizing biochemical reactions of the cells is possible by the method of the present invention. Accordingly, whether the cells are alive or not, the method of the present invention is applicable to various evaluations.

In addition, many types of cells can be cultured simultaneously by the animal cell-embedded culture-test method of the present invention, because the globular collagen gel is used in this method. If types or compositions (density or the like) of cells to be embedded in the gel are different between drops of the gel, interactions between the cells can be evaluated.

The animal cell-embedded culture-test method of the present invention is applicable to anticancer agent sensitivity tests, tests using co-culture, screening of new drugs, animal experiment substitution methods, performance tests of artificial organs, and the like.

We claim:
1. A method for culturing animal cells under embedded conditions, comprising the steps of dispersing animal cells into a collagen solution;
   placing at least one drop containing about 3 to about 300 microliters of said collagen solution on a surface of a support and allowing said at least one drop to gel to form and fix on the support surface a globular collagen gel having a convex surface; and
   contacting said collagen gel with a cell culture medium and culturing said animal cells.
2. A method as in claim 1, which further comprises evaluating cultured cells obtained by said culturing step.

3. A method as in claim 2, wherein the evaluating step includes contacting a biochemical reaction reagent with said cells embedded in the collagen gel.

4. A method as in claim 3, wherein said evaluating step further includes:

photographing the collagen gel to obtain an image and analyzing said image.

5. A method as in claim 4, wherein said image analyzing step further includes selectively staining the cells embedded in the collagen gel.

6. A method as in claim 5, wherein the staining step includes selectively staining live cells in the collagen gel.

7. A method as in claim 6, wherein the staining step includes selectively staining live cells in the collagen gel with a neutral red staining (NR-staining) agent.

8. A method as in claim 7, wherein the NR-staining step includes:

fixing the NR-staining agent into the lives in the cells; and drying the NR-staining agent fixed in the fixing step.

9. A method as in claim 8, wherein said animal cells which are cultured in the culture step are primary cells.

10. A method as in claim 9, which further comprises a step of preculturing a preliminary culture sample containing the animal cells in the culture medium on a surface of a preliminary support with a collagen gel layer as an adhesion factor prior to dispersing into said collagen solution, and collecting only live cells which are adhered to the surface of the preliminary support to obtain the culture sample.

11. A method as in claim 10, wherein the culture medium is a serum-free culture medium.

12. A method as in claim 10, wherein the primary cells are obtained from about 0.001 to 1 g of tissue.

13. A method as in claim 9, wherein the primary cells are obtained from about 0.001 to 1 g of tissue.

14. A method as in claim 6, further comprising staining said live cells with fluorescein diacetate and irradiating the stained cells with an amount of excitation light in a range of $1 \times 10^0$ to $1 \times 10^7$ lux-sec at a temperature in a range of 1° to 15° C.

15. A method as in claim 3, wherein said animal cells which are cultured are primary cells.

16. A method as in claim 15, which further comprises a step of preculturing a preliminary culture sample containing the animal cells on a surface of a preliminary support in the culture medium prior to dispersing said cells into said collagen solution, and collecting only live cells which are adhered to the surface of the preliminary support to obtain the culture sample.

17. A method as in claim 16, wherein the preliminary support has a surface coating of a cell adhesion factor.

18. A method as in claim 17, wherein the cell adhesion factor is a collagen gel layer.

19. A method as in claim 18, wherein the culture is a serum-free culture medium.

20. A method as in claim 18, wherein the primary cells are obtained from about 0.001 to 1 g of tissue.

21. A method as in claim 17, wherein the culture medium contains dextran sulfate.

22. A method as in claim 15, wherein the primary cells are obtained from about 0.001 to 1 g of tissue.

23. A method as in claim 3, wherein said evaluating step includes a step of colorimetric analysis using a coloring reagent to produce a selective color reaction by metabolic activity of the live cells in said collagen gel.

24. A method as in claim 3, wherein said evaluating step includes a step of quatitatively analyzing substances contained in the cells embedded in the collagen gel.

25. A method as in claim 3, wherein said evaluating step includes a step of quantitatively analyzing substances secreted into the culture medium from the cells embedded in the collagen gel.

26. A method as in claim 3, wherein said evaluating step includes selectively staining the cells embedded in the collagen gel, and extracting a reagent after the staining step.

27. A method as in claim 26, further comprising selectively staining live cells in the collagen gel.

28. The method of claim 1, wherein said support surface comprises a continuous ridge forming a recessed area, and said drop of collagen solution is placed in said recessed area to contain said globular collagen gel.

29. The method of claim 1, wherein said globular collagen gel has a height of about 2 mm or less.

* * * * *